US010093986B2

(12) United States Patent
Zhang et al.

(10) Patent No.: US 10,093,986 B2
(45) Date of Patent: Oct. 9, 2018

(54) LEUKEMIA METHYLATION MARKERS AND USES THEREOF

(71) Applicants: YouHealth Biotech, Limited, Grand Cayman (KY); The Regents of the University of California, Oakland, CA (US)

(72) Inventors: Kang Zhang, San Diego, CA (US); Rui Hou, Shenyang (CN); Lianghong Zheng, Shenyang (CN)

(73) Assignees: YOUHEALTH BIOTECH, LIMITED, Grand cayman (KY); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/435,174

(22) Filed: Feb. 16, 2017

(65) Prior Publication Data

US 2018/0010192 A1 Jan. 11, 2018

Related U.S. Application Data

(60) Provisional application No. 62/358,762, filed on Jul. 6, 2016.

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/106* (2013.01); *C12Q 2600/154* (2013.01)

(58) Field of Classification Search
None
See application file for complete search history.

(56) References Cited

U.S. PATENT DOCUMENTS

| | | |
|---|---|---|
| 4,683,202 A | 7/1987 | Mullis |
| 5,525,462 A | 6/1996 | Takarada et al. |
| 5,786,146 A | 7/1998 | Herman et al. |
| 5,972,602 A | 10/1999 | Hyland et al. |
| 6,017,704 A | 1/2000 | Herman et al. |
| 6,033,854 A | 3/2000 | Kurnit et al. |
| 6,114,117 A | 9/2000 | Hepp et al. |
| 6,127,120 A | 10/2000 | Graham et al. |
| 6,180,349 B1 | 1/2001 | Ginzinger et al. |
| 6,200,756 B1 | 3/2001 | Herman et al. |
| 6,265,171 B1 | 7/2001 | Herman et al. |
| 6,306,597 B1 | 10/2001 | MacEvicz |
| 6,331,393 B1 | 12/2001 | Laird et al. |
| 6,344,317 B2 | 2/2002 | Urnovitz |
| 6,448,001 B2 | 9/2002 | Oku et al. |
| 6,528,632 B1 | 3/2003 | Catanzariti et al. |
| 6,797,470 B2 | 9/2004 | Barany et al. |
| 7,011,944 B2 | 3/2006 | Prudent et al. |
| 7,037,687 B2 | 5/2006 | Williams et al. |
| 7,083,917 B2 | 8/2006 | Barany et al. |
| 7,166,434 B2 | 1/2007 | Barany et al. |
| 7,169,560 B2 | 1/2007 | Lapidus et al. |
| 7,186,512 B2 | 3/2007 | Martienssen et al. |
| 7,232,656 B2 | 6/2007 | Balasubramanian et al. |
| 7,320,865 B2 | 1/2008 | Barany et al. |
| 7,332,285 B2 | 2/2008 | Barany et al. |
| 7,364,858 B2 | 4/2008 | Barany et al. |
| 7,429,453 B2 | 9/2008 | Barany et al. |
| 7,459,274 B2 | 12/2008 | Lakey et al. |
| 7,553,627 B2 | 6/2009 | Laird et al. |
| 7,598,035 B2 | 10/2009 | MacEvicz |
| 7,611,869 B2 | 11/2009 | Fan |
| 7,645,596 B2 | 1/2010 | Williams et al. |
| 7,700,324 B1 | 4/2010 | Issa et al. |
| 7,769,400 B2 | 8/2010 | Backholm et al. |
| 7,901,880 B2 | 3/2011 | Jeddeloh et al. |
| 7,910,296 B2 | 3/2011 | Jeddeloh et al. |
| 8,323,890 B2 | 12/2012 | Laird et al. |
| 2005/0069879 A1 | 3/2005 | Berlin |
| 2009/0155791 A1 | 6/2009 | Wojdacz et al. |
| 2009/0203588 A1 | 8/2009 | Willman et al. |
| 2009/0264306 A1 | 10/2009 | Caldwell et al. |
| 2010/0144836 A1 | 6/2010 | Van et al. |
| 2011/0287968 A1 | 11/2011 | Weinhausel et al. |

FOREIGN PATENT DOCUMENTS

| | | |
|---|---|---|
| WO | WO-03064701 A2 | 8/2003 |
| WO | WO-2005012578 A1 | 2/2005 |
| WO | WO-2005111209 A1 | 11/2005 |
| WO | WO-2006056480 A2 | 6/2006 |
| WO | WO-2009021141 A1 | 2/2009 |
| WO | WO-2009049916 A2 | 4/2009 |
| WO | WO-2018009702 A1 | 1/2018 |

OTHER PUBLICATIONS

Milani et al, Blood 115 (6), 1214 (2010).*
Acevedo et al. Analysis of the mechanisms mediating tumor-specific changes in gene expression in human liver tumors. Cancer Res. 68:2641-2651 (2008).
Bair et al. Semi-supervised methods to predict patient survival from gene expression data. PLoS Biol 2(4):E108 (2004).
Balic et al. High quality assessment of DNA methylation in archival tissues from colorectal cancer patients using quantitative high-resolution melting analysis. J. Mol. Diagn. 11:102-108 (2009).
Ball et al. Targeted and genome-scale strategies reveal gene-body methylation signatures in human cells. Nat. Biotechnol 27:361-368 (2009).
Bettegowda et al. Detection of Circulating Tumor DNA in Early- and Late-Stage Human Malignancies. Sci. Transl. Med. 6(224):224ra24 (2014).
Bibkova et al. High-throughput DNA methylation profiling using universal bead arrays. Genome Res. 16:383-393 (2006).
Bo et al. New feature subset selection procedures for classification of expression profiles. Genome Biology 3(4):research0017.1-0017.11 (2002).

(Continued)

*Primary Examiner* — James Martinell
(74) *Attorney, Agent, or Firm* — Wilson, Sonsini, Goodrich & Rosati

(57) ABSTRACT

Disclosed herein are methods and kits for identifying a subject as having leukemia. Also provided herein are methods and kits for determining a leukemia subtype in subject. Further provided herein are methods and kits for determining the prognosis of a subject having leukemia and for determining the progression of leukemia in a subject.

21 Claims, 6 Drawing Sheets

(6 of 6 Drawing Sheet(s) Filed in Color)

(56) References Cited

OTHER PUBLICATIONS

Breiman. Random Forests. Machine Learning 45:5-32 (2001).
Candiloro et al. Assessing combined methylation-sensitive high resolution melting and pyrosequencing for the analysis of heterogeneous DNA methylation. Epigenetics 6(4):500-507 (2011).
Costello et al. Restriction landmark genome scanning. Meth. Mol Biol 200:53-70 (2002).
Cottrell et al. A real-time PCR assay for DNA-methylation using methylation-specific blockers. Nucleic Acids Res. 32:e10 (2004).
Cottrell et al. Discovery and validation of 3 novel DNA methylation markers of prostate cancer prognosis. J. Urology 177:1753-1758 (2007).
Degraves et al. High-Sensitivity Quantitative PCR Platform. Biotechniques 34(1):106-115 (2003).
Deiman et al. Characteristics and applications of nucleic acid sequence-based amplification (NASBA). Mol. Biotechnol. 20(2):163-179 (2002).
Deng et al. Targeted bisulfite sequencing reveals changes in DNA methylation associated with nuclear reprogramming. Nat. Biotechnol 27:353-360 (2009).
Diep et al. Library-free methylation sequencing with bisulfite padlock probes. Nature Methods 9(3):270-272 (2012).
Dudoit et al. Comparison of Discrimination Methods for the Classification of Tumors Using Gene Expression Data. Journal of the American Statistical Association 97:77-87 (2002).
Eads et al. MethyLight: a high-throughput assay to measure DNA methylation. Nucleic Acid Res. 28:e32 (2000).
Fackler et al. Quantitative multiplex methylation-specific PCR analysis doubles detection of tumor cells in breast ductal fluid. Clin. Cancer Res. 12(11 Pt 1):3306-3310 (2006).
Fackler et al. Quantitative multiplex methylation-specific PCR assay for the detection of promoter hypermethylation in multiple genes in breast cancer. Cancer Res. 64(13):4442-4452 (2004).
Friedman. Regularized Discriminant Analysis. Journal of the American Statistical Association 84:165-175 (1989).
Frommer et al. A genomic sequencing protocol that yields a positive display of 5-methylcytosine residues in individual DNA strands. PNAS USA 89:1827-1831 (1992).
Gebhard et al. Genome-wide profiling of CpG methylation identifies novel targets of aberrant hypermethylation in myeloid leukemia. Cancer Res. 66:6118-6128 (2006).
Gebhard et al. Rapid and sensitive detection of CpG-methylation using methyl-binding (MB)-PCR. Nucleic Acids Res. 34:e82 (2006).
Gibson et al. A novel method for real time quantitative RT-PCR. Genome Research 6:995-1001 (1996).
Gonzalgo et al. Rapid quantitation of methylation differences at specific sites using methylation-sensitive single nucleotide primer extension (Ms-SNuPE). Nucleic Acids Res. 25:2529-2531 (1997).
Harris et al. Single-molecule DNA sequencing of a viral genome. Science 320:106-109 (2008).
Herman et al. Methylation-specific PCR: a novel PCR assay for methylation status of CpG islands. PNAS USA 93:9821-9826 (1996).
Horak et al. ChIP-chip: a genomic approach for identifying transcription factor binding sites. Methods Enzymol 350:469-483 (2002).
Itzkowitz et al. Improved fecal DNA test for colorectal cancer screening. Clin Gastroenterol. Hepatol. 5(1):111-117 (2007).
Koga et al. Genome-wide screen of promoter methylation identifies novel markers in melanoma. Genome Res. 19:1462-1470 (2009).
Langmead et al. Fast gapped-read alignment with Bowtie 2. Nature Methods 9:357-359 (2012).
Lieb. Genome-wide mapping of protein-DNA interactions by chromatin immunoprecipitation and DNA microarray hybridization. Methods Mol Biol 224:99-109 (2003).
Margulies et al. Genome sequencing in microfabricated high-density picolitre reactors. Nature 437:376-380 (2005).
McClelland et al. Effect of site-specific modification on restriction endonucleases and DNA modification methyltransferases. Nucleic Acids Res. 22(17):3640-3659 (1994).
Nakano et al. Single-molecule PCR using water-in-oil emulsion. J. Biotech. 102:117-124 (2003).
Nolte. Branched DNA signal amplification for direct quantitation of nucleic acid sequences in clinical specimens. Adv. Clin. Chem. 33:201-235 (1998).
O'Geen et al. Comparison of sample preparation methods for ChIP-chip assays. BioTechniques 41(5):577-580 (2006).
Olek et al. The pre-implantation ontogeny of the H19 methylation imprint Nat. Genet. 17(3):275-276 (1997).
Pelizzola et al. MEDME: an experimental and analytical methodology for the estimation of DNA methylation levels based on microarray derived MeDIP-enrichment. Genome Res. 18:1652-1659 (2008).
Radmacher et al. A paradigm for class prediction using gene expression profiles. Journal of Computational Biology 9:505-511 (2002).
Ramaswamy et al. Multiclass cancer diagnosis using tumor gene expression signatures. PNAS USA 98:15149-15154 (2001).
Rauch et al. High-resolution mapping of DNA hypermethylation and hypomethylation in lung cancer. PNAS USA 105:252-257 (2008).
Rein et al. Identifying 5-methylcytosine and related modifications in DNA genomes. Nucleic Acids Res. 26(10):2255-2264 (1998).
Ruczinski et al. Logic Regression. Journal of Computational and Graphical Statistics 12:475-5111 (2003).
Sadri et al. Rapid analysis of DNA methylation using new restriction enzyme sites created by bisulfite modification. Nucleic Acids Res. 24:5058-5059 (1996).
Shiraishi et al. Isolation of DNA fragments associated with methylated CpG islands in human adenocarcinomas of the lung using a methylated DNA binding column and denaturing gradient gel electrophoresis. PNAS USA 96(6):2913-2918 (1999).
Simon et al. Pitfalls in the use of DNA microarray data for diagnostic and prognostic classification. Journal of the National Cancer Institute 95:14-18 (2003).
Soni et al. Progress toward ultrafast DNA sequencing using solid-state nanopores. Clin. Chem. 53:1996-2001 (2007).
Tibshirani et al. Class prediction by nearest shrunken centroids with applications to DNA microarrays. Statistical Science 18(1):104-117 (2003).
Tibshirani et al. Diagnosis of multiple cancer types by shrunken centroids of gene expression. PNAS 99:6567-6572 (2002).
Tost et al. DNA methylation analysis by pyrosequencing. Nature Protocols 2:2265-2275 (2007).
Toyota et al. Identification of differentially methylated sequences in colorectal cancer by methylated CpG island amplification. Cancer Res. 59:2307-2312 (1999).
Ushijima et al. Methylation-Sensitive Representational Difference Analysis (MS-RDA). Methods Mol Biol507:117-130 (2009).
Weber et al. Chromosome-wide and promoter-specific analyses identify sites of differential DNA methylation in normal and transformed human cells. Nat. Genet. 37:853-862 (2005).
Wojdacz et al. Methylation-sensitive high resolution melting (MS-HRM): a new approach for sensitive and high-throughput assessment of methylation. Nucleic Acids Res. 35(6):e41 (2007).
Wojdacz et al. Methylation-sensitive high-resolution melting. Nature Protocols 3(12):1903-1908 (2008).
Wright et al. A random variance model for detection of differential gene expression in small microarray experiments. Bioinformatics 19(18):2448-2455 (2003).
Xiong et al Cobra: a sensitive and quantitative DNA methylation assay. Nucleic Acids Res. 25:2532-2534 (1997).
Zou et al. Association of Clinical Chemistry (AACC) poster presentation on Jul. 28, 2010. Sensitive Quantification of Methylated Markers with a Novel Methylation Specific Technology. Available at www.exactsciences.com.
PCT/US2017/040953 Invitation to Pay Additional Fees dated Oct. 10, 2017.
Byun et al. Impact of Chromosomal Rearrangement upon DNA Methylation Patterns in Leukemia. Open Med (Wars) 12:76-85 (2017).

(56) References Cited

OTHER PUBLICATIONS

Hao et al. DNA methylation markers for diagnosis and prognosis of common cancers. PNAS USA 114(28):7414-7419 (w/Supplemental Information) (2017.
Johnson et al. DNA methylation in ductal carcinoma in situ related with future development of invasive breast cancer. Clin Epigenetics 7:75 (2015).
PCT/US2017/040953 International Search Report and Written Opinion dated Dec. 5, 2017.

* cited by examiner

FIG. 5A
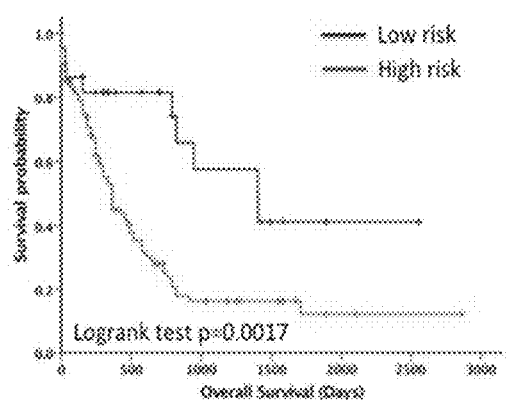
FIG. 5B
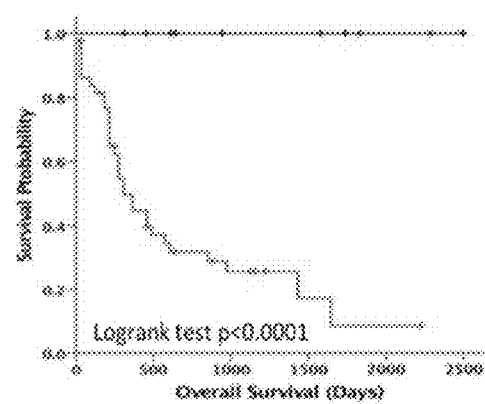
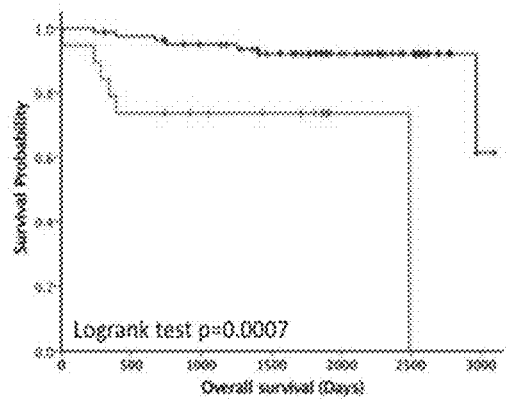
FIG. 5C
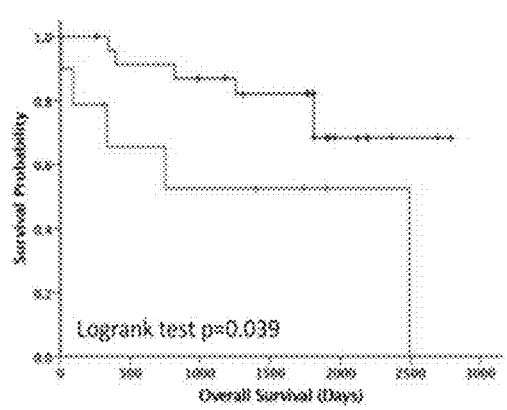
FIG. 5D

LEUKEMIA METHYLATION MARKERS AND USES THEREOF

CROSS-REFERENCE

This application claims the benefit of U.S. Provisional Application No. 62/358,762, filed Jul. 6, 2016, which application is incorporated herein by reference.

BACKGROUND OF THE DISCLOSURE

Leukemia belongs to a group of blood cancers that also includes lymphoma and myeloma. Diagnostic procedures for leukemia, in some cases, begin only after a patient is already present with symptoms, leading to costly, invasive, and sometimes time-consuming procedures. In addition, inaccessible areas sometimes prevent an accurate diagnosis. Further, high cancer morbidities and mortalities are associated with late diagnosis.

SUMMARY OF THE DISCLOSURE

Provided herein are methods and kits for identifying a subject as having leukemia. Also provided herein are methods and kits for determining a leukemia subtype in subject. Further provided herein are methods and kits for determining the prognosis of a subject having leukemia and for determining the progression of leukemia in a subject.

In certain embodiments, provided herein is a method of selecting a subject suspected of having leukemia for treatment, the method comprising: (a) processing an extracted genomic DNA with a deaminating agent to generate a genomic DNA sample comprising deaminated nucleotides, wherein the extracted genomic DNA is obtained from a biological sample from the subject suspected of having leukemia; (b) generating a methylation profile comprising one or more biomarkers selected from: cg08261841, cg09247255, cg00142402, cg16274678, and cg02381853 from the extracted genomic DNA; (c) comparing the methylation profile of the one or more biomarkers with a control; (d) identifying the subject as having leukemia if the methylation profile correlates to the control; and (e) administering an effective amount of a therapeutic agent to the subject if the subject is identified as having leukemia.

In some embodiments, the methylation profile comprises cg08261841, cg09247255, cg00142402, cg16274678, and cg02381853.

In some embodiments, the method further comprises generating a methylation profile comprising a biomarker selected from: cg05304729, cg00484711, cg18518074, cg05048927, cg08960448, and cg12008047. In some embodiments, the methylation profile comprises cg08261841, cg09247255, cg00142402, cg16274678, cg0238185, cg05304729, cg00484711, cg18518074, cg05048927, cg08960448, and cg12008047.

In some embodiments, the comparing further comprises generating a pair-wise methylation difference dataset comprising: (i) a first difference between the methylation profile of the treated genomic DNA with a methylation profile of a first normal sample; (ii) a second difference between a methylation profile of a second normal sample and a methylation profile of a third normal sample; and (iii) a third difference between a methylation profile of a first primary cancer sample and a methylation profile of a second primary cancer sample.

In some embodiments, the comparing further comprises analyzing the pair-wise methylation difference dataset with a control by a machine learning method to generate the methylation profile.

In some embodiments, the first primary cancer sample is a leukemia sample. In some embodiments, the second primary cancer sample is a non-leukemia cancer sample.

In some embodiments, the control comprises a set of methylation profiles, wherein each said methylation profile is generated from a biological sample obtained from a known cancer type.

In some embodiments, the known cancer type is leukemia. In some embodiments, the known cancer type is a relapsed or refractory leukemia. In some embodiments, the known cancer type is a metastatic leukemia.

In some embodiments, the machine learning method utilizes an algorithm selected from one or more of the following: a principal component analysis, a logistic regression analysis, a nearest neighbor analysis, a support vector machine, and a neural network model.

In some embodiments, the generating further comprises hybridizing each of the one or more biomarkers with a probe, and performing a DNA sequencing reaction to quantify the methylation of each of the one or more biomarkers.

In some embodiments, the biological sample comprises a blood sample. In some embodiments, the biological sample comprises a tissue biopsy sample. In some embodiments, the biological sample comprises circulating tumor cells.

In some embodiments, the subject is a human.

In certain embodiments, provided herein is a method of determining a leukemia subtype in a subject in need thereof, comprising: (a) processing an extracted genomic DNA with a deaminating agent to generate a genomic DNA sample comprising deaminated nucleotides, wherein the extracted genomic DNA is obtained from a biological sample from the subject; (b) generating a methylation profile comprising biomarkers cg08261841, cg09247255, cg12008047, cg00142402, cg16274678, cg02381853, cg05304729, cg00484711, cg18518074, cg05048927, and cg08960448 from the extracted genomic DNA; (c) comparing the methylation profile of the biomarkers with a control; (d) based on the methylation profile of the biomarkers relative to the control, identify a leukemia subtype in the subject; and (e) administering a tailored therapeutic regimen to treat the subject having the leukemia subtype.

In some embodiments, the comparing further comprises generating a pair-wise methylation difference dataset comprising: (i) a first difference between the methylation profile of the treated genomic DNA with a methylation profile of a first normal sample; (ii) a second difference between a methylation profile of a second normal sample and a methylation profile of a third normal sample; and (iii) a third difference between a methylation profile of a first leukemia subtype sample and a methylation profile of a second leukemia subtype sample.

In some embodiments, the comparing further comprises analyzing the pair-wise methylation difference dataset with a control by a machine learning method to generate the methylation profile.

In some embodiments, the control comprises a set of methylation profiles, wherein each said methylation profile is generated from a biological sample obtained from a known leukemia subtype.

In some embodiments, the leukemia subtype comprises acute lymphoblastic leukemia (ALL), acute myeloid leukemia (AML), chronic lymphocytic leukemia (CLL), chronic myeloid leukemia (CML), hairy cell leukemia (HCL), chronic myelomonocytic leukemia (CMML), juvenile myelomonocytic leukemia (JMML), large granular lymphocytic leukemia (LGL), or blastic plasmacytoid dendritic cell neoplasm (BPDCN). In some embodiments, the leukemia subtype comprises acute lymphoblastic leukemia (ALL) or acute myeloid leukemia (AML). In some embodiments, the leukemia subtype is a relapsed or refractory leukemia subtype. In some embodiments, the leukemia subtype is a metastatic leukemia subtype.

In some embodiments, the machine learning method utilizes an algorithm selected from one or more of the following: a principal component analysis, a logistic regression analysis, a nearest neighbor analysis, a support vector machine, and a neural network model.

In some embodiments, the generating further comprises hybridizing each of the one or more biomarkers with a probe, and performing a DNA sequencing reaction to quantify the methylation of each of the one or more biomarkers.

In some embodiments, the biological sample comprises a blood sample. In some embodiments, the biological sample comprises a tissue biopsy sample. In some embodiments, the biological sample comprises circulating tumor cells.

In some embodiments, the subject is a human.

In certain embodiments, provided herein is a method of determining if a subject has acute lymphoblastic leukemia (ALL), comprising: (a) processing an extracted genomic DNA with a deaminating agent to generate a genomic DNA sample comprising deaminated nucleotides, wherein the extracted genomic DNA is obtained from a biological sample from the subject; (b) generating a methylation profile comprising biomarkers cg08261841, cg09247255, cg12008047, cg05304729, cg18518074, cg05048927, and cg08960448 from the extracted genomic DNA; (c) comparing the methylation profile of the biomarkers with a methylation profile of a normal sample; (d) based on the methylation profile of the biomarkers relative to the methylation profile of the normal sample, identify whether the subject has ALL; and (e) administering a tailored therapeutic regimen to treat the subject if the subject has ALL.

In certain embodiments, provided herein is a method of determining if a subject has acute myeloid leukemia (AML), comprising: (a) processing an extracted genomic DNA with a deaminating agent to generate a genomic DNA sample comprising deaminated nucleotides, wherein the extracted genomic DNA is obtained from a biological sample from the subject; (b) generating a methylation profile comprising biomarkers cg00142402, cg05304729, cg00484711, and cg18518074 from the extracted genomic DNA; (c) comparing the methylation profile of the biomarkers with a methylation profile of a normal sample; (d) based on the methylation profile of the biomarkers relative to the methylation profile of the normal sample, identify whether the subject has AML; and (e) administering a tailored therapeutic regimen to treat the subject if the subject has AML.

In certain embodiments, provided herein is a method of distinguishing between acute lymphoblastic leukemia and acute myeloid leukemia in a subject in need thereof, comprising: (a) processing an extracted genomic DNA with a deaminating agent to generate a genomic DNA sample comprising deaminated nucleotides, wherein the extracted genomic DNA is obtained from a biological sample from the subject; (b) generating a methylation profile comprising biomarkers cg08261841, cg09247255, cg00142402, cg16274678, and cg02381853 from the extracted genomic DNA; (c) comparing the methylation profile of the biomarkers with a control; (d) based on the methylation profile of the biomarkers relative to the control, identify whether the subject has acute lymphoblastic leukemia or acute myeloid leukemia; and (e) administering a tailored therapeutic regimen to treat the subject based on the subject having acute lymphoblastic leukemia or acute myeloid leukemia.

In certain embodiments, provided herein is a method of generating a methylation profile of a biomarker in a subject in need thereof, comprising: (a) processing an extracted genomic DNA with a deaminating agent to generate a genomic DNA sample comprising deaminated nucleotides, wherein the extracted genomic DNA is obtained from a biological sample from the subject; (b) detecting a hybridization between the extracted genomic DNA and a probe, wherein the probe hybridizes to a biomarker selected from cg08261841, cg09247255, cg00142402, cg16274678, and cg02381853; and (c) generating a methylation profile based on the detected hybridization between the extracted genomic DNA and the probe.

In some embodiments, the methylation profile comprises cg08261841, cg09247255, cg00142402, cg16274678, and cg02381853.

In some embodiments, the method further comprises generating a methylation profile comprising a biomarker selected from: cg05304729, cg00484711, cg18518074, cg05048927, cg08960448, and cg12008047. In some embodiments, the methylation profile comprises cg08261841, cg09247255, cg00142402, cg16274678, cg0238185, cg05304729, cg00484711, cg18518074, cg05048927, cg08960448, and cg12008047.

In some embodiments, the generating further comprises generating a pair-wise methylation difference dataset comprising: (i) a first difference between the methylation profile of the treated genomic DNA with a methylation profile of a first normal sample; (ii) a second difference between a methylation profile of a second normal sample and a methylation profile of a third normal sample; and (iii) a third difference between a methylation profile of a first primary cancer sample and a methylation profile of a second primary cancer sample.

In some embodiments, the generating further comprises analyzing the pair-wise methylation difference dataset with a control by a machine learning method to generate the methylation profile.

In some embodiments, the first primary cancer sample is a leukemia sample. In some embodiments, the second primary cancer sample is a non-leukemia cancer sample.

In some embodiments, the control comprises a set of methylation profiles, wherein each said methylation profile is generated from a biological sample obtained from a known cancer type.

In some embodiments, the known cancer type is leukemia. In some embodiments, the known cancer type is a relapsed or refractory leukemia. In some embodiments, the known cancer type is a metastatic leukemia. In some embodiments, the known cancer type is acute lymphoblastic leukemia (ALL), acute myeloid leukemia (AML), chronic lymphocytic leukemia (CLL), chronic myeloid leukemia (CML), hairy cell leukemia (HCL), chronic myelomonocytic leukemia (CMML), juvenile myelomonocytic leukemia (JMML), large granular lymphocytic leukemia (LGL), or blastic plasmacytoid dendritic cell neoplasm (BPDCN).

In some embodiments, the machine learning method utilizes an algorithm selected from one or more of the following: a principal component analysis, a logistic regression analysis, a nearest neighbor analysis, a support vector machine, and a neural network model.

In some embodiments, the method further comprises performing a DNA sequencing reaction to quantify the methylation of each of the one or more biomarkers prior to generating the methylation profile.

In some embodiments, the biological sample comprises a blood sample. In some embodiments, the biological sample comprises a tissue biopsy sample. In some embodiments, the biological sample comprises circulating tumor cells.

In some embodiments, the subject is a human.

In certain embodiments, provided herein is a method of determining the prognosis of a subject having acute myeloid leukemia or monitoring the progression of acute myeloid leukemia in the subject, comprising: (a) processing an extracted genomic DNA with a deaminating agent to generate a genomic DNA sample comprising deaminated nucleotides, wherein the extracted genomic DNA is obtained from a biological sample from the subject having acute myeloid leukemia; (b) generating a methylation profile comprising one or more biomarkers selected from: cg01336231, cg01413582, cg01509330, cg02264990, cg02329430, cg02858512, cg03297901, cg03556653, cg04596071, cg05038216, cg06034933, cg08098128, cg13066703, cg17757602, cg18869709, cg19966212, cg20300129, cg23193870, cg23680451, and cg25145765 from the extracted genomic DNA; (c) obtaining a methylation score based on the methylation profile of the one or more biomarkers; and (d) based on the methylation score, initiate a first treatment, decrease a dosage of a first therapeutic agent if the subject has experienced a remission, initiate a second treatment if the subject has experienced a relapse, or switch to a second therapeutic agent if the subject becomes refractory to the first therapeutic agent.

In some embodiments, the methylation profile comprises cg01336231, cg01413582, cg01509330, cg02264990, cg02329430, cg02858512, cg03297901, cg03556653, cg04596071, cg05038216, cg06034933, cg08098128, cg13066703, cg17757602, cg18869709, cg19966212, cg20300129, cg23193870, cg23680451, and cg25145765.

In some embodiments, the methylation score of from about 1.5 to about 3 is indicative of a survival for at least 6 months. In some embodiments, the methylation score of from about 1.5 to about 3 is indicative of a survival for at least 1 year. In some embodiments, the methylation score of from about 1.5 to about 3 is indicative of a survival for at least 1.5 years. In some embodiments, the methylation score of from about 1.5 to about 3 is indicative of a survival for at least 2 years. In some embodiments, the methylation score of from about 1.5 to about 3 is indicative of a survival for at least 2.5 years. In some embodiments, the methylation score of from about 1.5 to about 3 is indicative of a survival for at least 3 years. In some embodiments, the methylation score of from about 1.5 to about 3 is indicative of a survival for at least 4 years. In some embodiments, the methylation score of from about 1.5 to about 3 is indicative of a survival for at least 5 years.

In some embodiments, the methylation score of from about 1.5 to about 2.5 is indicative of a survival for at least 6 months. In some embodiments, the methylation score of from about 1.5 to about 2.5 is indicative of a survival for at least 1 year. In some embodiments, the methylation score of from about 1.5 to about 2.5 is indicative of a survival for at least 1.5 years. In some embodiments, the methylation score of from about 1.5 to about 2.5 is indicative of a survival for at least 2 years. In some embodiments, the methylation score of from about 1.5 to about 2.5 is indicative of a survival for at least 2.5 years. In some embodiments, the methylation score of from about 1.5 to about 2.5 is indicative of a survival for at least 3 years. In some embodiments, the methylation score of from about 1.5 to about 2.5 is indicative of a survival for at least 4 years. In some embodiments, the methylation score of from about 1.5 to about 2.5 is indicative of a survival for at least 5 years.

In some embodiments, the methylation score of less than 1.5 is indicative of a survival of less than 5 years. In some embodiments, the methylation score of less than 1.5 is indicative of a survival of less than 4 years. In some embodiments, the methylation score of less than 1.5 is indicative of a survival of less than 3 years. In some embodiments, the methylation score of less than 1.5 is indicative of a survival of less than 2.5 years. In some embodiments, the methylation score of less than 1.5 is indicative of a survival of less than 2 years. In some embodiments, the methylation score of less than 1.5 is indicative of a survival of less than 1.5 years. In some embodiments, the methylation score of less than 1.5 is indicative of a survival of less than 1 year. In some embodiments, the methylation score of less than 1.5 is indicative of a survival of less than 6 months.

In some embodiments, the methylation score is calculated based on Cox proportional hazards (PH) regression analysis.

In some embodiments, acute myeloid leukemia is metastatic acute myeloid leukemia.

In some embodiments, the generating further comprises hybridizing each of the one or more biomarkers with a probe, and performing a DNA sequencing reaction to quantify the methylation of each of the one or more biomarkers.

In some embodiments, the biological sample comprises a blood sample. In some embodiments, the biological sample comprises a tissue biopsy sample. In some embodiments, the biological sample comprises circulating tumor cells.

In some embodiments, the subject is a human.

In certain embodiments, provided herein is a method of determining the prognosis of a subject having acute lymphoblastic leukemia or monitoring the progression of acute lymphoblastic leukemia in the subject, comprising: (a) processing an extracted genomic DNA with a deaminating agent to generate a genomic DNA sample comprising deaminated nucleotides, wherein the extracted genomic DNA is obtained from a biological sample from the subject suspected of having acute myeloid leukemia; (b) generating a methylation profile comprising one or more biomarkers selected from: cg01628067, cg03001333, cg04984818, cg05145233, cg05304729, cg05956452, cg06261066, cg09157302, cg14608384, cg15289427, cg15608301, cg15707093, cg16266227, cg18869709, cg19470372, cg19864130, cg20686234, cg21913319, cg24720672, cg24747122, cg24983367, cg26584619, and cg27178401 from the extracted genomic DNA; (c) obtaining a methylation score based on the methylation profile of the one or more biomarkers; and (d) based on the methylation score, initiate a first treatment, decrease a dosage of a first therapeutic agent if the subject has experienced a remission, initiate a second treatment if the subject has experienced a relapse, or switch to a second therapeutic agent if the subject becomes refractory to the first therapeutic agent.

In some embodiments, the methylation profile comprises cg01628067, cg03001333, cg04984818, cg05145233, cg05304729, cg05956452, cg06261066, cg09157302, cg14608384, cg15289427, cg15608301, cg15707093, cg16266227, cg18869709, cg19470372, cg19864130, cg20686234, cg21913319, cg24720672, cg24747122, cg24983367, cg26584619, and cg27178401.

In some embodiments, the methylation score of from about 1.5 to about 3 is indicative of a survival for at least 6 months. In some embodiments, the methylation score of from about 1.5 to about 3 is indicative of a survival for at least 1 year. In some embodiments, the methylation score of from about 1.5 to about 3 is indicative of a survival for at least 1.5 years. In some embodiments, the methylation score of from about 1.5 to about 3 is indicative of a survival for at least 2 years. In some embodiments, the methylation score of from about 1.5 to about 3 is indicative of a survival for at least 2.5 years. In some embodiments, the methylation score of from about 1.5 to about 3 is indicative of a survival for at least 3 years. In some embodiments, the methylation score of from about 1.5 to about 3 is indicative of a survival for at least 4 years. In some embodiments, the methylation score of from about 1.5 to about 3 is indicative of a survival for at least 5 years.

In some embodiments, the methylation score of from about 1.5 to about 2.5 is indicative of a survival for at least 6 months. In some embodiments, the methylation score of from about 1.5 to about 2.5 is indicative of a survival for at least 1 year. In some embodiments, the methylation score of from about 1.5 to about 2.5 is indicative of a survival for at least 1.5 years. In some embodiments, the methylation score of from about 1.5 to about 2.5 is indicative of a survival for at least 2 years. In some embodiments, the methylation score of from about 1.5 to about 2.5 is indicative of a survival for at least 2.5 years. In some embodiments, the methylation score of from about 1.5 to about 2.5 is indicative of a survival for at least 3 years. In some embodiments, the methylation score of from about 1.5 to about 2.5 is indicative of a survival for at least 4 years. In some embodiments, the methylation score of from about 1.5 to about 2.5 is indicative of a survival for at least 5 years.

In some embodiments, the methylation score of less than 1.5 is indicative of a survival of less than 5 years. In some embodiments, the methylation score of less than 1.5 is indicative of a survival of less than 4 years. In some embodiments, the methylation score of less than 1.5 is indicative of a survival of less than 3 years. In some embodiments, the methylation score of less than 1.5 is indicative of a survival of less than 2.5 years. In some embodiments, the methylation score of less than 1.5 is indicative of a survival of less than 2 years. In some embodiments, the methylation score of less than 1.5 is indicative of a survival of less than 1.5 years. In some embodiments, the methylation score of less than 1.5 is indicative of a survival of less than 1 year. In some embodiments, the methylation score of less than 1.5 is indicative of a survival of less than 6 months.

In some embodiments, the methylation score is calculated based on Cox proportional hazards (PH) regression analysis.

In some embodiments, acute lymphoblastic leukemia is metastatic acute lymphoblastic leukemia.

In some embodiments, the generating further comprises hybridizing each of the one or more biomarkers with a probe, and performing a DNA sequencing reaction to quantify the methylation of each of the one or more biomarkers.

In some embodiments, the biological sample comprises a blood sample. In some embodiments, the biological sample comprises a tissue biopsy sample. In some embodiments, the biological sample comprises circulating tumor cells.

In some embodiments, the subject is a human.

In certain embodiments, provided herein is a kit comprising a set of nucleic acid probes that hybridizes to biomarkers: cg08261841, cg09247255, cg12008047, cg00142402, cg16274678, cg0238185, cg05304729, cg00484711, cg18518074, cg05048927, and cg08960448. In some embodiments, the set of nucleic acid probes comprises a set of padlock probes.

In certain embodiments, provided herein is a kit comprising a set of nucleic acid probes that hybridizes to biomarkers: cg01336231, cg01413582, cg01509330, cg02264990, cg02329430, cg02858512, cg03297901, cg03556653, cg04596071, cg05038216, cg06034933, cg08098128, cg13066703, cg17757602, cg18869709, cg19966212, cg20300129, cg23193870, cg23680451, and cg25145765. In some embodiments, the set of nucleic acid probes comprises a set of padlock probes.

In certain embodiments, provided herein is a kit comprising a set of nucleic acid probes that hybridizes to biomarkers: cg01628067, cg03001333, cg04984818, cg05145233, cg05304729, cg05956452, cg06261066, cg09157302, cg14608384, cg15289427, cg15608301, cg15707093, cg16266227, cg18869709, cg19470372, cg19864130, cg20686234, cg21913319, cg24720672, cg24747122, cg24983367, cg26584619, and cg27178401. In some embodiments, the set of nucleic acid probes comprises a set of padlock probes.

BRIEF DESCRIPTION OF THE DRAWINGS

The patent or applications file contains at least one drawing executed in color. Copies of this patent or patent application publication with color drawing(s) will be provided by the office upon request and payment of the necessary fee.

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1A shows the methylation profile of four markers which illustrates the differences between AML and normal blood. Unsupervised hierarchical clustering and heat map associated with the methylation profile (according to the color scale shown) in AML vs normal blood (TCGA DATA). FIG. 1B shows the ROC curve calculated based on the four markers in FIG. 1A.

FIG. 2A shows the methylation profile of seven markers which illustrates the differences between ALL and normal blood. Unsupervised hierarchical clustering and heat maps associated with the methylation profile (according to the color scale shown) in ALL versus normal blood samples. FIG. 2B shows the ROC curve calculated based on the 7 markers in FIG. 2A.

FIG. 3B shows a sensitivity vs. specificity plot in which the AUC is 0.9998.

FIG. 5A-FIG. 5D illustrate five-year overall survival of patients based on methylation markers. FIG. 5A shows the five-year overall survival probability of patients in the AML training set. FIG. 5B shows the five-year overall survival probability of patients in the AML validation set. FIG. 5C shows the five-year overall survival probability of patients in the ALL training set. FIG. 5D shows the five-year overall survival probability of patients in the ALL validation set.

FIG. 6A shows the five-year overall survival probability of patients with AML. FIG. 6B shows the five-year overall survival probability of patients with ALL.

DETAILED DESCRIPTION OF THE DISCLOSURE

Figure 1A:
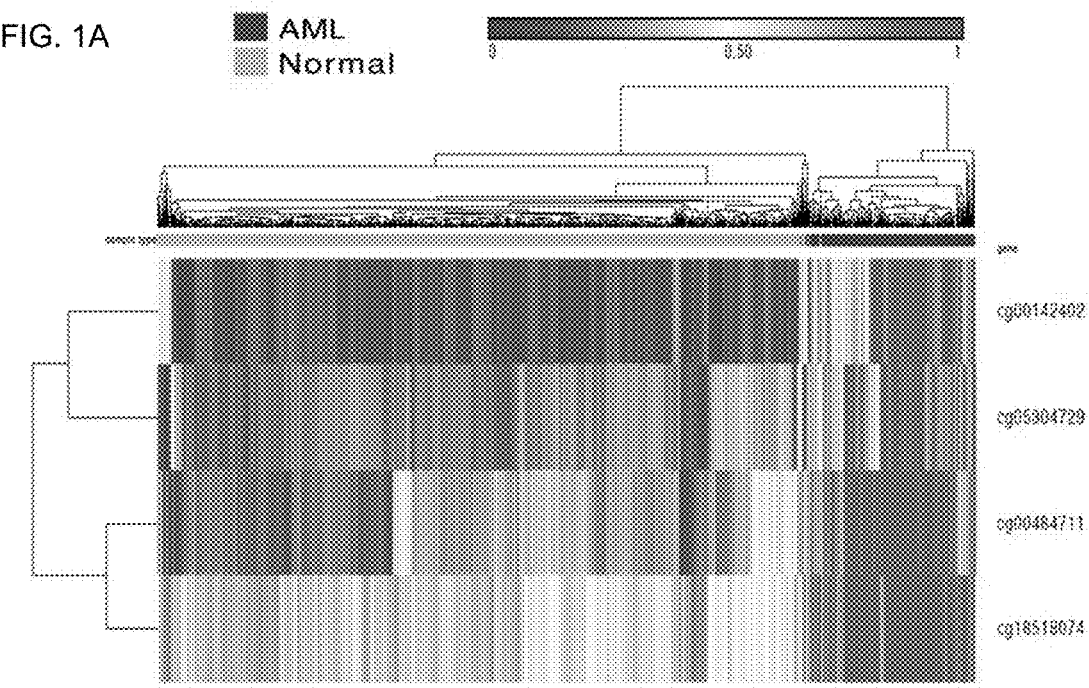
FIG. 1A-FIG. 1B illustrate a methylation profile of AML in comparison to normal blood.

Cancer is characterized by an abnormal growth of a cell caused by one or more mutations or modifications of a gene leading to dysregulated balance of cell proliferation and cell death. DNA methylation silences expression of tumor suppression genes, and presents itself as one of the first neoplastic changes. Methylation patterns found in neoplastic tissue and plasma demonstrate homogeneity, and in some instances are utilized as a sensitive diagnostic marker. For example, cMethDNA assay has been shown in one study to be about 91% sensitive and about 96% specific when used to diagnose metastatic breast cancer. In another study, circulating tumor DNA (ctDNA) was about 87.2% sensitive and about 99.2% specific when it was used to identify KRAS gene mutation in a large cohort of patients with metastatic colon cancer (Bettegowda et al., Detection of Circulating Tumor DNA in Early- and Late-Stage Human Malignancies. Sci. Transl. Med, 6(224):ra24. 2014). The same study further demonstrated that ctDNA is detectable in >75% of patients with advanced pancreatic, ovarian, colorectal, bladder, gastroesophageal, breast, melanoma, hepatocellular, and head and neck cancers (Bettegowda et al).

Additional studies have demonstrated that CpG methylation pattern correlates with neoplastic progression. For example, in one study of breast cancer methylation patterns, P16 hypermethylation has been found to correlate with early stage breast cancer, while TIMP3 promoter hypermethylation has been correlated with late stage breast cancer. In addition, BMP6, CST6 and TIMP3 promoter hypermethylation have been shown to associate with metastasis into lymph nodes in breast cancer.

In some embodiments, DNA methylation profiling provides higher clinical sensitivity and dynamic range compared to somatic mutation analysis for cancer detection. In other instances, altered DNA methylation signature has been shown to correlate with the prognosis of treatment response for certain cancers. For example, one study illustrated that in a group of patients with advanced rectal cancer, ten differentially methylated regions were used to predict patients' prognosis. Likewise, RASSF1A DNA methylation measurement in serum was used to predict a poor outcome in patients undergoing adjuvant therapy in breast cancer patients in a different study. In addition, SRBC gene hypermethylation was associated with poor outcome in patients with colorectal cancer treated with oxaliplatin in a different study. Another study has demonstrated that ESR1 gene methylation correlate with clinical response in breast cancer patients receiving tamoxifen. Additionally, ARHI gene promoter hypermethylation was shown to be a predictor of long-term survival in breast cancer patients not treated with tamoxifen.

Leukemia comprises a group of hematopoietic cell disorders arising from the lymphoid or myeloid lineage or from hematopoietic stem cells. In some instances, diagnosis of leukemia and leukemia subtype comprises immunological and/or molecular based classifications or histological identifications.

In some embodiments, disclosed herein are methods and kits of diagnosing leukemia and/or leukemia subtypes based on DNA methylation profiling. In some instances, provided herein are methods and kits of identifying a subject has having leukemia based on the DNA methylation profiling. In some instances, also provided herein are methods and kits of determining a leukemia subtype based on DNA methylation profiling. In some instances, further provided herein are methods and kits of determining the prognosis of a subject having leukemia and determining the progression of leukemia in a subject based on the DNA methylation profilings.

Methods of Use
Methods of Diagnosis of a Subject

Disclosed herein, in certain embodiments, are methods of diagnosing leukemia and selecting subjects suspected of having leukemia for treatment. In some instances, the methods comprise utilizing one or more biomarkers described herein. In some instances, a biomarker comprises a cytosine methylation site. In some instances, cytosine methylation comprises 5-methylcytosine (5-mCyt) and 5-hydroxymethylcytosine. In some cases, a cytosine methylation site occurs in a CpG dinucleotide motif. In other cases, a cytosine methylation site occurs in a CHG or CHH motif, in which H is adenine, cytosine, or thymine. In some instances, one or more CpG dinucleotide motif or CpG site forms a CpG island, a short DNA sequence rich in CpG dinucleotide. In some instances, CpG islands are typically, but not always, between about 0.2 to about 1 kb in length. In some instances, a biomarker comprises a CpG island.

In some embodiments, disclosed herein is a method of selecting a subject suspected of having leukemia for treatment, in which the method comprises (a) processing an extracted genomic DNA with a deaminating agent to generate a genomic DNA sample comprising deaminated nucleotides, wherein the extracted genomic DNA is obtained from a biological sample from the subject suspected of having leukemia; (b) generating a methylation profile comprising one or more biomarkers selected from: cg08261841, cg09247255, cg00142402, cg16274678, and cg02381853 from the extracted genomic DNA; (c) comparing the methylation profile of the one or more biomarkers with a control; (d) identifying the subject as having leukemia if the methylation profile correlates to the control; and (e) administering an effective amount of a therapeutic agent to the subject if the subject is identified as having leukemia.

In some embodiments, a methylation profile comprises a plurality of CpG methylation data for one or more biomarkers described herein. In some instances, a plurality of CpG methylation data is generated by first obtaining a genomic DNA (e.g., nuclear DNA or circulating DNA) from a biological sample, and then treating the genomic DNA by a deaminating agent to generate an extracted genomic DNA. In some instances, the extracted genomic DNA (e.g., extracted nuclear DNA or extracted circulating DNA) is optionally treated with one or more restriction enzymes to generate a set of DNA fragments prior to submitting for sequencing analysis to generate CpG methylation data. In some cases, the sequencing analysis comprises hybridizing each of the one or more biomarkers described herein with a probe, and performing a DNA sequencing reaction to quantify the methylation of each of the one or more biomarkers. In some instances, the CpG methylation data is then input into a machine learning/classification program to generate a methylation profile.

In some instances, a set of biological samples are generated and subsequently input into the machine learning/classification program. In some instances, the set of biological samples comprises 2, 3, 4, 5, 6, 7, 8, 9, 10, 20, 30, or more biological samples. In some instances, the set of biological samples comprises 2, 3, 4, 5, 6, 7, 8, 9, 10, 20, 30, or more normal biological samples. In some instances, the set of biological samples comprises 2, 3, 4, 5, 6, 7, 8, 9, 10, 20, 30, or more cancerous biological samples. In some cases, the set of biological samples comprise a biological sample of interest, a first primary cancer sample, a second primary cancer sample, a first normal sample, a second normal sample, and a third normal sample; wherein the first, and second primary cancer samples are different; and wherein the first, second, and third normal samples are different. In some cases, three pairs of difference datasets are generated in which the three pairs of dataset comprise: a first difference dataset between the methylation profile of the biological sample of interest and the first normal sample, in which the biological sample of interest and the first normal sample are from the same biological sample source; a second difference dataset between a methylation profile of a second normal sample and a methylation profile of a third normal sample, in which the second and third normal samples are different; and a third difference dataset between a methylation profile of a first primary cancer sample and a methylation profile of a second primary cancer sample, in which the first and second primary cancer samples are different. In some instances, the difference datasets are further input into the machine learning/classification program. In some cases, a pair-wise methylation difference dataset from the first, second, and third datasets is generated and then analyzed in the presence of a control dataset or a training dataset by the machine learning/classification method to generate the cancer CpG methylation profile. In some instances, the first primary cancer sample is a leukemia sample. In some cases, the second primary cancer sample is a non-leukemia cancer sample. In some cases, the machine learning method comprises identifying a plurality of markers and a plurality of weights based on a top score (e.g., a t-test value, a β test value), and classifying the samples based on the plurality of markers and the plurality of weights. In some cases, the machine learning method utilizes an algorithm selected from one or more of the following: a principal component analysis, a logistic regression analysis, a nearest neighbor analysis, a support vector machine, and a neural network model.

In some embodiments, the CpG methylation profile comprises one or more biomarkers selected from: cg08261841, cg09247255, cg12008047, cg00142402, cg16274678, cg0238185, cg05304729, cg00484711, cg18518074, cg05048927, and cg08960448. In some embodiments, the CpG methylation profile comprises two or more biomarkers selected from: cg08261841, cg09247255, cg12008047, cg00142402, cg16274678, cg0238185, cg05304729, cg00484711, cg18518074, cg05048927, and cg08960448. In some embodiments, the CpG methylation profile comprises three or more biomarkers selected from: cg08261841, cg09247255, cg12008047, cg00142402, cg16274678, cg0238185, cg05304729, cg00484711, cg18518074, cg05048927, and cg08960448. In some embodiments, the CpG methylation profile comprises four or more biomarkers selected from: cg08261841, cg09247255, cg12008047, cg00142402, cg16274678, cg0238185, cg05304729, cg00484711, cg18518074, cg05048927, and cg08960448. In some embodiments, the CpG methylation profile comprises five or more biomarkers selected from: cg08261841, cg09247255, cg12008047, cg00142402, cg16274678, cg0238185, cg05304729, cg00484711, cg18518074, cg05048927, and cg08960448. In some embodiments, the CpG methylation profile comprises six or more biomarkers selected from: cg08261841, cg09247255, cg12008047, cg00142402, cg16274678, cg0238185, cg05304729, cg00484711, cg18518074, cg05048927, and cg08960448. In some embodiments, the CpG methylation profile comprises seven or more biomarkers selected from: cg08261841, cg09247255, cg12008047, cg00142402, cg16274678, cg0238185, cg05304729, cg00484711, cg18518074, cg05048927, and cg08960448. In some embodiments, the CpG methylation profile comprises eight or more biomarkers selected from: cg08261841, cg09247255, cg12008047, cg00142402, cg16274678, cg0238185, cg05304729, cg00484711, cg18518074, cg05048927, and cg08960448. In some embodiments, the CpG methylation profile comprises nine or more biomarkers selected from: cg08261841, cg09247255, cg12008047, cg00142402, cg16274678, cg0238185, cg05304729, cg00484711, cg18518074, cg05048927, and cg08960448. In some embodiments, the CpG methylation profile comprises ten or more biomarkers selected from: cg08261841, cg09247255, cg12008047, cg00142402, cg16274678, cg0238185, cg05304729, cg00484711, cg18518074, cg05048927, and cg08960448. In some embodiments, the CpG methylation profile comprises cg08261841, cg09247255, cg12008047, cg00142402, cg16274678, cg0238185, cg05304729, cg00484711, cg18518074, cg05048927, and cg08960448.

In some instances, the CpG methylation profile comprises one or more biomarkers selected from: cg08261841, cg09247255, cg00142402, cg16274678, and cg02381853. In some instances, the CpG methylation profile comprises two or more biomarkers selected from: cg08261841, cg09247255, cg00142402, cg16274678, and cg02381853. In some instances, the CpG methylation profile comprises three or more biomarkers selected from: cg08261841, cg09247255, cg00142402, cg16274678, and cg02381853. In some instances, the CpG methylation profile comprises four or more biomarkers selected from: cg08261841, cg09247255, cg00142402, cg16274678, and cg02381853. In some instances, the CpG methylation profile comprises cg08261841, cg09247255, cg00142402, cg16274678, and cg02381853.

In some instances, the CpG methylation profile comprises one or more biomarkers selected from: cg08261841, cg09247255, cg00142402, cg16274678, and cg02381853; and one or more biomarkers selected from: cg05304729, cg00484711, cg18518074, cg05048927, cg08960448, and cg12008047.

In some instances, the subject is diagnosed in having leukemia. Leukemia encompasses a family of blood cancers. In some instances, leukemia further comprises a relapsed or refractory leukemia. In other instances, leukemia comprises a metastatic leukemia. In some cases, the subject is diagnosed in having a relapsed or refractory leukemia. In additional cases, the subject is diagnosed in having a metastatic leukemia.

In some embodiments, the subject diagnosed of having leukemia is further treated with a therapeutic agent. Exemplary therapeutic agents include, but are not limited to, alemtuzumab, arsenic trioxide, bendamustine, blinatumomab, bosutinib, busulfan, clofarabine, chlorambucil, cyclophosphamide, cytarabine, daunorubicin hydrochloride, dasatinib, doxorubicin, fludarabine, ibrutinib, idarubicin hydrochloride, imatinib mesylate, mercaptopurine, methotrexate, nelarabine, nilotinib, ofatumumab, pegasparagase, prednisone, recombinant interferon Alfa-2b, rituximab, venetoclax, vincristine, or a combination thereof.

In some embodiments, also described herein include a method of generating a methylation profile of a biomarker. In some instances, the method comprises (a) processing an extracted genomic DNA with a deaminating agent to generate a genomic DNA sample comprising deaminated nucleotides, wherein the extracted genomic DNA is obtained from a biological sample from the subject; (b) detecting a hybridization between the extracted genomic DNA and a probe, wherein the probe hybridizes to a biomarker selected from cg08261841, cg09247255, cg00142402, cg16274678, and cg02381853; and (c) generating a methylation profile based on the detected hybridization between the extracted genomic DNA and the probe.

In some embodiments, one or more biomarkers selected from: cg08261841, cg09247255, cg12008047, cg00142402, cg16274678, cg0238185, cg05304729, cg00484711, cg18518074, cg05048927, and cg08960448 are used to generate a methylation profile. In some embodiments, two or more, three or more, four or more, five or more, six or more, seven or more, eight or more, nine or more, or ten or more biomarkers selected from: cg08261841, cg09247255, cg12008047, cg00142402, cg16274678, cg0238185, cg05304729, cg00484711, cg18518074, cg05048927, and cg08960448 are used to generate the methylation profile. In some embodiments, cg08261841, cg09247255, cg12008047, cg00142402, cg16274678, cg0238185, cg05304729, cg00484711, cg18518074, cg05048927, and cg08960448 are used to generate a methylation profile.

In some instances, as described elsewhere herein, a pairwise methylation difference dataset is generated prior to generating a methylation profile. In some cases, the pairwise methylation difference dataset comprises (i) a first difference between the methylation profile of the treated genomic DNA with a methylation profile of a first normal sample; (ii) a second difference between a methylation profile of a second normal sample and a methylation profile of a third normal sample; and (iii) a third difference between a methylation profile of a first primary cancer sample and a methylation profile of a second primary cancer sample.

In some cases, the pair-wise methylation difference dataset is analyzed with a control by a machine learning method to generate a methylation profile. In some cases, the machine learning method utilizes an algorithm selected from one or more of the following: a principal component analysis, a logistic regression analysis, a nearest neighbor analysis, a support vector machine, and a neural network model.

In some embodiments, a probe comprises a DNA probe, RNA probe, or a combination thereof. In some instances, a probe comprises natural nucleic acid molecules and non-natural nucleic acid molecules. In some cases, a probe comprises a labeled probe, such as for example, fluorescently labeled probe or radioactively labeled probe. In some instances, a probe correlates to a CpG site. In some instances, a probe is utilized in a next generation sequencing reaction to generate a CpG methylation data. In further instances, a probe is used in a solution-based next generation sequencing reaction to generate a CpG methylation data. In some cases, a probe comprises a molecular beacon probe, a TaqMan probe, locked nucleic acid probe, a padlock probe, or Scorpion probe. In some cases, a probe comprises a padlock probe.

In some cases, the method further comprises performing a DNA sequencing reaction such as those described elsewhere herein to quantify the methylation of each of the one or more biomarkers prior to generating a methylation profile.

Methods of Determining a Leukemia Subtype

In some embodiments, disclosed herein include a method of determining a leukemia subtype. In some embodiments, a leukemia subtype comprises acute lymphoblastic leukemia (ALL), acute myeloid leukemia (AML), chronic lymphocytic leukemia (CLL), chronic myeloid leukemia (CML), hairy cell leukemia (HCL), chronic myelomonocytic leukemia (CMML), juvenile myelomonocytic leukemia (JMML), large granular lymphocytic leukemia (LGL), or blastic plasmacytoid dendritic cell neoplasm (BPDCN).

In some instances, a subject is diagnosed in having a leukemia subtype: acute lymphoblastic leukemia (ALL), acute myeloid leukemia (AML), chronic lymphocytic leukemia (CLL), chronic myeloid leukemia (CML), hairy cell leukemia (HCL), chronic myelomonocytic leukemia (CMML), juvenile myelomonocytic leukemia (JMML), large granular lymphocytic leukemia (LGL), or blastic plasmacytoid dendritic cell neoplasm (BPDCN) based on the methylation profile of a sample obtained from the subject. In some instances, a subject is diagnosed in having acute lymphoblastic leukemia (ALL) based on the methylation profile of a sample obtained from the subject. In some instances, a subject is diagnosed in having acute myeloid leukemia (AML) based on the methylation profile of a sample obtained from the subject. In some instances, a subject is diagnosed in having chronic lymphocytic leukemia (CLL) based on the methylation profile of a sample obtained from the subject. In some instances, a subject is diagnosed in having chronic myeloid leukemia (CML) based on the methylation profile of a sample obtained from the subject. In some instances, a subject is diagnosed in having hairy cell leukemia (HCL) based on the methylation profile of a sample obtained from the subject. In some instances, a subject is diagnosed in having chronic myelomonocytic leukemia (CMML) based on the methylation profile of a sample obtained from the subject. In some instances, a subject is diagnosed in having juvenile myelomonocytic leukemia (JMML) based on the methylation profile of a sample obtained from the subject. In some instances, a subject is diagnosed in having large granular lymphocytic leukemia (LGL) based on the methylation profile of a sample obtained from the subject. In some instances, a subject is diagnosed in having blastic plasmacytoid dendritic cell neoplasm (BPDCN) based on the methylation profile of a sample obtained from the subject.

In some embodiments, a leukemia subtype also comprises a relapsed or refractory leukemia subtype or a metastatic leukemia subtype. In some embodiments, a subject is diagnosed in having a relapsed or refractory leukemia subtype based on the methylation profile of a sample obtained from the subject. In other embodiments, a subject is diagnosed in having a metastatic leukemia subtype based on the methylation profile of a sample obtained from the subject.

In some embodiments, described herein is a method of determining a leukemia subtype in a subject in need thereof, comprising (a) processing an extracted genomic DNA with a deaminating agent to generate a genomic DNA sample comprising deaminated nucleotides, wherein the extracted genomic DNA is obtained from a biological sample from the subject; (b) generating a methylation profile comprising biomarkers cg08261841, cg09247255, cg12008047, cg00142402, cg16274678, cg02381853, cg05304729, cg00484711, cg18518074, cg05048927, and cg08960448 from the extracted genomic DNA; (c) comparing the methylation profile of the biomarkers with a control; (d) based on the methylation profile of the biomarkers relative to the control, identify a leukemia subtype in the subject; and (e) administering a tailored therapeutic regimen to treat the subject having the leukemia subtype.

In some instances, a pair-wise methylation difference dataset is generated prior to generating the methylation profile. In some cases, the pair-wise methylation difference dataset comprises (i) a first difference between the methylation profile of the treated genomic DNA with a methylation profile of a first normal sample; (ii) a second difference between a methylation profile of a second normal sample and a methylation profile of a third normal sample; and (iii) a third difference between a methylation profile of a first leukemia subtype sample and a methylation profile of a second leukemia subtype sample.

In some cases, the pair-wise methylation difference dataset is analyzed with a control by a machine learning method to generate a methylation profile. In some cases, the machine learning method utilizes an algorithm selected from one or more of the following: a principal component analysis, a logistic regression analysis, a nearest neighbor analysis, a support vector machine, and a neural network model.

In some cases, the method further comprises hybridizing each of the one or more biomarkers with a probe, and performing a DNA sequencing reaction to quantify the methylation of each of the one or more biomarkers. In some instances, a probe comprises a DNA probe, RNA probe, or a combination thereof. In some instances, a probe comprises natural nucleic acid molecules and non-natural nucleic acid molecules. In some cases, a probe comprises a labeled probe, such as for example, fluorescently labeled probe or radioactively labeled probe. In some instances, a probe correlates to a CpG site. In some instances, a probe is utilized in a next generation sequencing reaction to generate a CpG methylation data. In further instances, a probe is used in a solution-based next generation sequencing reaction to generate a CpG methylation data. In some cases, a probe comprises a molecular beacon probe, a TaqMan probe, locked nucleic acid probe, a padlock probe, or Scorpion probe. In some cases, a probe comprises a padlock probe.

In some embodiments, the subject is further treated with a therapeutic agent. Exemplary therapeutic agents include, but are not limited to, alemtuzumab, arsenic trioxide, bendamustine, blinatumomab, bosutinib, busulfan, clofarabine, chlorambucil, cyclophosphamide, cytarabine, daunorubicin hydrochloride, dasatinib, doxorubicin, fludarabine, ibrutinib, idarubicin hydrochloride, imatinib mesylate, mercaptopurine, methotrexate, nelarabine, nilotinib, ofatumumab, pegaspargase, prednisone, recombinant interferon Alfa-2b, rituximab, venetoclax, vincristine, or a combination thereof.

In some embodiments, disclosed herein is a method of determining if a subject has acute lymphoblastic leukemia (ALL). Acute lymphoblastic leukemia (ALL), also known as acute lymphocytic leukemia or acute lymphoid leukemia, is characterized by an overproduction and accumulation of cancerous immature lymphoblasts. In some instances, overproduced cancerous lymphoblasts in the bone marrow deplete production of normal red blood cells, normal white blood cells and/or platelets, and sometimes further infiltrates surrounding organs.

In some embodiments, disclosed herein is a method of determining if a subject has ALL which comprises (a) processing an extracted genomic DNA with a deaminating agent to generate a genomic DNA sample comprising deaminated nucleotides, wherein the extracted genomic DNA is obtained from a biological sample from the subject; (b) generating a methylation profile comprising biomarkers cg08261841, cg09247255, cg12008047, cg05304729, cg18518074, cg05048927, and cg08960448 from the extracted genomic DNA; (c) comparing the methylation profile of the biomarkers with a methylation profile of a normal sample; (d) based on the methylation profile of the biomarkers relative to the methylation profile of the normal sample, identify whether the subject has ALL; and (e) administering a tailored therapeutic regimen to treat the subject if the subject has ALL.

In some instances, a pair-wise methylation difference dataset is generated prior to generating the methylation profile. In some cases, the pair-wise methylation difference dataset comprises (i) a first difference between the methylation profile of the treated genomic DNA with a methylation profile of a first normal sample; (ii) a second difference between a methylation profile of a second normal sample and a methylation profile of a third normal sample; and (iii) a third difference between a methylation profile of a first leukemia subtype sample and a methylation profile of a second leukemia subtype sample.

In some cases, the pair-wise methylation difference dataset is analyzed with a control by a machine learning method to generate a methylation profile. In some cases, the machine learning method utilizes an algorithm selected from one or more of the following: a principal component analysis, a logistic regression analysis, a nearest neighbor analysis, a support vector machine, and a neural network model.

In some cases, the method further comprises hybridizing each of the one or more biomarkers with a probe, and performing a DNA sequencing reaction to quantify the methylation of each of the one or more biomarkers. As described above, a probe sometimes comprises a DNA probe, RNA probe, or a combination thereof. In some instances, a probe comprises natural nucleic acid molecules and non-natural nucleic acid molecules. In some cases, a probe comprises a labeled probe, such as for example, fluorescently labeled probe or radioactively labeled probe. In some instances, a probe correlates to a CpG site. In some instances, a probe is utilized in a next generation sequencing reaction to generate a CpG methylation data. In further instances, a probe is used in a solution-based next generation sequencing reaction to generate a CpG methylation data. In some cases, a probe comprises a molecular beacon probe, a TaqMan probe, locked nucleic acid probe, a padlock probe, or Scorpion probe. In some cases, a probe comprises a padlock probe.

In some embodiments, the subject is further treated with a therapeutic agent. Exemplary therapeutic agents include, but are not limited to, chemotherapeutic agents such as prednisolone, dexamethasone, vincristine, asparaginase, daunorubicin, cytarabine and methotrexate combination, or liposomal cytarabine; retinoids such as all-trans retinoic acid (ATRA); radiation; or biologics such as blinatumomab (a CD19-CD3 bi-specific monoclonal antibody).

In some embodiments, the subject is further treated with a stem cell transplant upon diagnosis of having ALL.

In some embodiments, also disclosed herein is a method of determining if a subject has acute myeloid leukemia (AML). Acute myeloid leukemia, also known as acute myelogenous leukemia or acute nonlymphocytic leukemia (ANLL), is a cancer of the myeloid line of blood cells. Similar to ALL, overproduced cancerous myeloid cells within the bone marrow decrease the production of normal cells such as white or red blood cells and/or platelets and sometimes infiltrate surrounding organs. In some instances, AML is further sub-classified into 8 subtypes: acute myeloblastic leukemia, minimally differentiated (M0 subtype); acute myeloblastic leukemia, without maturation (M1 subtype); acute myeloblastic leukemia, with granulocytic maturation (M2 subtype); promyelocytic or acute promyelocytic leukemia (APL) (M3 subtype); acute myelomonocytic leukemia (M4 subtype); myelomonocytic together with bone marrow eosinophilia (M4eo subtype); acute monoblastic leukemia (M5a subtype); acute monocytic leukemia (M5b subtype); acute erythroid leukemia, including erythroleukemia (M6a subtype); acute erythroid leukemia with pure erythroid leukemia (M6b subtype); and acute megakaryoblastic leukemia (M7 subtype).

In some embodiments, disclosed herein is a method of determining if a subject has AML, which comprises (a) processing an extracted genomic DNA with a deaminating agent to generate a genomic DNA sample comprising deaminated nucleotides, wherein the extracted genomic DNA is obtained from a biological sample from the subject; (b) generating a methylation profile comprising biomarkers cg00142402, cg05304729, cg00484711, and cg18518074 from the extracted genomic DNA; (c) comparing the methylation profile of the biomarkers with a methylation profile of a normal sample; (d) based on the methylation profile of the biomarkers relative to the methylation profile of the normal sample, identify whether the subject has AML; and (e) administering a tailored therapeutic regimen to treat the subject if the subject has AML.

In some instances, a pair-wise methylation difference dataset is generated prior to generating the methylation profile. In some cases, the pair-wise methylation difference dataset comprises (i) a first difference between the methylation profile of the treated genomic DNA with a methylation profile of a first normal sample; (ii) a second difference between a methylation profile of a second normal sample and a methylation profile of a third normal sample; and (iii) a third difference between a methylation profile of a first leukemia subtype sample and a methylation profile of a second leukemia subtype sample.

In some cases, the pair-wise methylation difference dataset is analyzed with a control by a machine learning method to generate a methylation profile. In some cases, the machine learning method utilizes an algorithm selected from one or more of the following: a principal component analysis, a logistic regression analysis, a nearest neighbor analysis, a support vector machine, and a neural network model.

In some cases, the method further comprises hybridizing each of the one or more biomarkers with a probe, and performing a DNA sequencing reaction to quantify the methylation of each of the one or more biomarkers. In some instances, a probe comprises a DNA probe, RNA probe, or a combination thereof. In some instances, a probe comprises natural nucleic acid molecules and non-natural nucleic acid molecules. In some cases, a probe comprises a labeled probe, such as for example, fluorescently labeled probe or radioactively labeled probe. In some instances, a probe correlates to a CpG site. In some instances, a probe is utilized in a next generation sequencing reaction to generate a CpG methylation data. In further instances, a probe is used in a solution-based next generation sequencing reaction to generate a CpG methylation data. In some cases, a probe comprises a molecular beacon probe, a TaqMan probe, locked nucleic acid probe, a padlock probe, or Scorpion probe. In some cases, a probe comprises a padlock probe.

In some embodiments, the subject is further treated with a therapeutic agent. Exemplary therapeutic agents include, but are not limited to, chemotherapeutic agents such as prednisolone, dexamethasone, vincristine, asparaginase, daunorubicin, cytaraine, cytarabine and methotrexate combination, or liposomal cytarabine; chemotherapeutic agent in combination with an anthracycline (e.g., daunorubicin); retinoids such as all-trans retinoic acid (ATRA); or radiation.

In some embodiments, the subject is further treated with a stem cell transplant upon diagnosis of having AML.

In some embodiments, disclosed herein is a method of distinguishing between acute lymphoblastic leukemia and acute myeloid leukemia in a subject in need thereof, comprising (a) processing an extracted genomic DNA with a deaminating agent to generate a genomic DNA sample comprising deaminated nucleotides, wherein the extracted genomic DNA is obtained from a biological sample from the subject; (b) generating a methylation profile comprising biomarkers cg08261841, cg09247255, cg00142402, cg16274678, and cg02381853 from the extracted genomic DNA; (c) comparing the methylation profile of the biomarkers with a control; (d) based on the methylation profile of the biomarkers relative to the control, identify whether the subject has acute lymphoblastic leukemia or acute myeloid leukemia; and (e) administering a tailored therapeutic regimen to treat the subject based on the subject having acute lymphoblastic leukemia or acute myeloid leukemia.

In some instances, a pair-wise methylation difference dataset is generated prior to generating the methylation profile. In some cases, the pair-wise methylation difference dataset comprises (i) a first difference between the methylation profile of the treated genomic DNA with a methylation profile of a first normal sample; (ii) a second difference between a methylation profile of a second normal sample and a methylation profile of a third normal sample; and (iii) a third difference between a methylation profile of a first leukemia subtype sample and a methylation profile of a second leukemia subtype sample.

In some cases, the pair-wise methylation difference dataset is analyzed with a control by a machine learning method to generate a methylation profile. In some cases, the machine learning method utilizes an algorithm selected from one or more of the following: a principal component analysis, a logistic regression analysis, a nearest neighbor analysis, a support vector machine, and a neural network model.

In some cases, the method further comprises hybridizing each of the one or more biomarkers with a probe, and performing a DNA sequencing reaction to quantify the methylation of each of the one or more biomarkers. In some instances, a probe comprises a DNA probe, RNA probe, or a combination thereof. In some instances, a probe comprises natural nucleic acid molecules and non-natural nucleic acid molecules. In some cases, a probe comprises a labeled probe, such as for example, fluorescently labeled probe or radioactively labeled probe. In some instances, a probe correlates to a CpG site. In some instances, a probe is utilized in a next generation sequencing reaction to generate a CpG methylation data. In further instances, a probe is used in a solution-based next generation sequencing reaction to generate a CpG methylation data. In some cases, a probe comprises a molecular beacon probe, a TaqMan probe, locked nucleic acid probe, a padlock probe, or Scorpion probe. In some cases, a probe comprises a padlock probe.

In some instances, a tailored therapeutic regimen comprises a treatment regimen applicable to a subject diagnosed in having ALL or AML. In some cases, a tailored therapeutic regimen comprises a treatment regimen applicable to a subject diagnosed in having ALL. In some cases, a tailored therapeutic regimen comprises one or more therapeutic agents for treatment of ALL. In some cases, a tailored therapeutic regimen comprises one or more therapeutic agents, including, but not limited to, chemotherapeutic agents such as prednisolone, dexamethasone, vincristine, asparaginase, daunorubicin, cytarabine and methotrexate combination, or liposomal cytarabine; retinoids such as all-trans retinoic acid (ATRA); radiation; or biologics such as blinatumomab (a CD19-CD3 bi-specific monoclonal antibody). In other cases, a tailored therapeutic regimen comprises a treatment regimen applicable to a subject diagnosed in having AML. In some cases, a tailored therapeutic regimen comprises one or more therapeutic agents for treatment of AML. In some cases, a tailored therapeutic regimen comprises one or more therapeutic agents, including, but not limited to, chemotherapeutic agents such as prednisolone, dexamethasone, vincristine, asparaginase, daunorubicin, cytaraine, cytarabine and methotrexate combination, or liposomal cytarabine; chemotherapeutic agent in combination with an anthracycline (e.g., daunorubicin); retinoids such as all-trans retinoic acid (ATRA); or radiation.

Determining the Prognosis of a Subject Having Leukemia or Monitoring the Progression of Leukemia in a Subject In some embodiments, disclosed herein include a method of determining the prognosis of a subject having leukemia or monitoring the progression of leukemia in a subject. In some instances, leukemia comprises acute myeloid leukemia or acute lymphoblastic leukemia. In some instances, disclosed herein is a method of determining the prognosis of a subject having acute myeloid leukemia or monitoring the progression of acute myeloid leukemia in a subject. In some embodiments, the method comprises (a) processing an extracted genomic DNA with a deaminating agent to generate a genomic DNA sample comprising deaminated nucleotides, wherein the extracted genomic DNA is obtained from a biological sample from the subject having acute myeloid leukemia; (b) generating a methylation profile comprising one or more biomarkers selected from: cg01336231, cg01413582, cg01509330, cg02264990, cg02329430, cg02858512, cg03297901, cg03556653, cg04596071, cg05038216, cg06034933, cg08098128, cg13066703, cg17757602, cg18869709, cg19966212, cg20300129, cg23193870, cg23680451, and cg25145765 from the extracted genomic DNA; (c) obtaining a methylation score based on the methylation profile of the one or more biomarkers; and (d) based on the methylation score, initiate a first treatment, decrease a dosage of a first therapeutic agent if the subject has experienced a remission, initiate a second treatment if the subject has experienced a relapse, or switch to a second therapeutic agent if the subject becomes refractory to the first therapeutic agent.

In some instances, the methylation profile comprises two or more biomarkers selected from: cg01336231, cg01413582, cg01509330, cg02264990, cg02329430, cg02858512, cg03297901, cg03556653, cg04596071, cg05038216, cg06034933, cg08098128, cg13066703, cg17757602, cg18869709, cg19966212, cg20300129, cg23193870, cg23680451, and cg25145765. In some instances, the methylation profile comprises three or more biomarkers selected from: cg01336231, cg01413582, cg01509330, cg02264990, cg02329430, cg02858512, cg03297901, cg03556653, cg04596071, cg05038216, cg06034933, cg08098128, cg13066703, cg17757602, cg18869709, cg19966212, cg20300129, cg23193870, cg23680451, and cg25145765. In some instances, the methylation profile comprises four or more biomarkers selected from: cg01336231, cg01413582, cg01509330, cg02264990, cg02329430, cg02858512, cg03297901, cg03556653, cg04596071, cg05038216, cg06034933, cg08098128, cg13066703, cg17757602, cg18869709, cg19966212, cg20300129, cg23193870, cg23680451, and cg25145765. In some instances, the methylation profile comprises five or more biomarkers selected from: cg01336231, cg01413582, cg01509330, cg02264990, cg02329430, cg02858512, cg03297901, cg03556653, cg04596071, cg05038216, cg06034933, cg08098128, cg13066703, cg17757602, cg18869709, cg19966212, cg20300129, cg23193870, cg23680451, and cg25145765. In some instances, the methylation profile comprises six or more biomarkers selected from: cg01336231, cg01413582, cg01509330, cg02264990, cg02329430, cg02858512, cg03297901, cg03556653, cg04596071, cg05038216, cg06034933, cg08098128, cg13066703, cg17757602, cg18869709, cg19966212, cg20300129, cg23193870, cg23680451, and cg25145765. In some instances, the methylation profile comprises seven or more biomarkers selected from: cg01336231, cg01413582, cg01509330, cg02264990, cg02329430, cg02858512, cg03297901, cg03556653, cg04596071, cg05038216, cg06034933, cg08098128, cg13066703, cg17757602, cg18869709, cg19966212, cg20300129, cg23193870, cg23680451, and cg25145765. In some instances, the methylation profile comprises eight or more biomarkers selected from: cg01336231, cg01413582, cg01509330, cg02264990, cg02329430, cg02858512, cg03297901, cg03556653, cg04596071, cg05038216, cg06034933, cg08098128, cg13066703, cg17757602, cg18869709, cg19966212, cg20300129, cg23193870, cg23680451, and cg25145765. In some instances, the methylation profile comprises nine or more biomarkers selected from: cg01336231, cg01413582, cg01509330, cg02264990, cg02329430, cg02858512, cg03297901, cg03556653, cg04596071, cg05038216, cg06034933, cg08098128, cg13066703, cg17757602, cg18869709, cg19966212, cg20300129, cg23193870, cg23680451, and cg25145765. In some instances, the methylation profile comprises ten or more biomarkers selected from: cg01336231, cg01413582, cg01509330, cg02264990, cg02329430, cg02858512, cg03297901, cg03556653, cg04596071, cg05038216, cg06034933, cg08098128, cg13066703, cg17757602, cg18869709, cg19966212, cg20300129, cg23193870, cg23680451, and cg25145765. In some instances, the methylation profile comprises eleven or more biomarkers selected from: cg01336231, cg01413582, cg01509330, cg02264990, cg02329430, cg02858512, cg03297901, cg03556653, cg04596071, cg05038216, cg06034933, cg08098128, cg13066703, cg17757602, cg18869709, cg19966212, cg20300129, cg23193870, cg23680451, and cg25145765. In some instances, the methylation profile comprises twelve or more biomarkers selected from: cg01336231, cg01413582, cg01509330, cg02264990, cg02329430, cg02858512, cg03297901, cg03556653, cg04596071, cg05038216, cg06034933, cg08098128, cg13066703, cg17757602, cg18869709, cg19966212, cg20300129, cg23193870, cg23680451, and cg25145765. In some instances, the methylation profile comprises fifteen or more biomarkers selected from: cg01336231, cg01413582, cg01509330, cg02264990, cg02329430, cg02858512, cg03297901, cg03556653, cg04596071, cg05038216, cg06034933, cg08098128, cg13066703, cg17757602, cg18869709, cg19966212, cg20300129, cg23193870, cg23680451, and cg25145765. In some instances, the methylation profile comprises cg01336231, cg01413582, cg01509330, cg02264990, cg02329430, cg02858512, cg03297901, cg03556653, cg04596071, cg05038216, cg06034933, cg08098128, cg13066703, cg17757602, cg18869709, cg19966212, cg20300129, cg23193870, cg23680451, and cg25145765.

In some instances, disclosed herein is a method of determining the prognosis of a subject having acute lymphoblastic leukemia or monitoring the progression of acute lymphoblastic leukemia in a subject. In some embodiments, the method comprises (a) processing an extracted genomic DNA with a deaminating agent to generate a genomic DNA sample comprising deaminated nucleotides, wherein the extracted genomic DNA is obtained from a biological sample from the subject suspected of having acute myeloid leukemia; (b) generating a methylation profile comprising one or more biomarkers selected from: cg01628067, cg03001333, cg04984818, cg05145233, cg05304729, cg05956452, cg06261066, cg09157302, cg14608384, cg15289427, cg15608301, cg15707093, cg16266227, cg18869709, cg19470372, cg19864130, cg20686234, cg21913319, cg24720672, cg24747122, cg24983367, cg26584619, and cg27178401 from the extracted genomic DNA; (c) obtaining a methylation score based on the methylation profile of the one or more biomarkers; and (d) based on the methylation score, initiate a first treatment, decrease a dosage of a first therapeutic agent if the subject has experienced a remission, initiate a second treatment if the subject has experienced a relapse, or switch to a second therapeutic agent if the subject becomes refractory to the first therapeutic agent.

In some instances, the methylation profile comprises two or more biomarkers selected from: cg01628067, cg03001333, cg04984818, cg05145233, cg05304729, cg05956452, cg06261066, cg09157302, cg14608384, cg15289427, cg15608301, cg15707093, cg16266227, cg18869709, cg19470372, cg19864130, cg20686234, cg21913319, cg24720672, cg24747122, cg24983367, cg26584619, and cg27178401. In some instances, the methylation profile comprises three or more biomarkers selected from: cg01628067, cg03001333, cg04984818, cg05145233, cg05304729, cg05956452, cg06261066, cg09157302, cg14608384, cg15289427, cg15608301, cg15707093, cg16266227, cg18869709, cg19470372, cg19864130, cg20686234, cg21913319, cg24720672, cg24747122, cg24983367, cg26584619, and cg27178401. In some instances, the methylation profile comprises four or more biomarkers selected from: cg01628067, cg03001333, cg04984818, cg05145233, cg05304729, cg05956452, cg06261066, cg09157302, cg14608384, cg15289427, cg15608301, cg15707093, cg16266227, cg18869709, cg19470372, cg19864130, cg20686234, cg21913319, cg24720672, cg24747122, cg24983367, cg26584619, and cg27178401. In some instances, the methylation profile comprises five or more biomarkers selected from: cg01628067, cg03001333, cg04984818, cg05145233, cg05304729, cg05956452, cg06261066, cg09157302, cg14608384, cg15289427, cg15608301, cg15707093, cg16266227, cg18869709, cg19470372, cg19864130, cg20686234, cg21913319, cg24720672, cg24747122, cg24983367, cg26584619, and cg27178401. In some instances, the methylation profile comprises six or more biomarkers selected from: cg01628067, cg03001333, cg04984818, cg05145233, cg05304729, cg05956452, cg06261066, cg09157302, cg14608384, cg15289427, cg15608301, cg15707093, cg16266227, cg18869709, cg19470372, cg19864130, cg20686234, cg21913319, cg24720672, cg24747122, cg24983367, cg26584619, and cg27178401. In some instances, the methylation profile comprises seven or more biomarkers selected from: cg01628067, cg03001333, cg04984818, cg05145233, cg05304729, cg05956452, cg06261066, cg09157302, cg14608384, cg15289427, cg15608301, cg15707093, cg16266227, cg18869709, cg19470372, cg19864130, cg20686234, cg21913319, cg24720672, cg24747122, cg24983367, cg26584619, and cg27178401. In some instances, the methylation profile comprises eight or more biomarkers selected from: cg01628067, cg03001333, cg04984818, cg05145233, cg05304729, cg05956452, cg06261066, cg09157302, cg14608384, cg15289427, cg15608301, cg15707093, cg16266227, cg18869709, cg19470372, cg19864130, cg20686234, cg21913319, cg24720672, cg24747122, cg24983367, cg26584619, and cg27178401. In some instances, the methylation profile comprises nine or more biomarkers selected from: cg01628067, cg03001333, cg04984818, cg05145233, cg05304729, cg05956452, cg06261066, cg09157302, cg14608384, cg15289427, cg15608301, cg15707093, cg16266227, cg18869709, cg19470372, cg19864130, cg20686234, cg21913319, cg24720672, cg24747122, cg24983367, cg26584619, and cg27178401. In some instances, the methylation profile comprises ten or more biomarkers selected from: cg01628067, cg03001333, cg04984818, cg05145233, cg05304729, cg05956452, cg06261066, cg09157302, cg14608384, cg15289427, cg15608301, cg15707093, cg16266227, cg18869709, cg19470372, cg19864130, cg20686234, cg21913319, cg24720672, cg24747122, cg24983367, cg26584619, and cg27178401. In some instances, the methylation profile comprises eleven or more biomarkers selected from: cg01628067, cg03001333, cg04984818, cg05145233, cg05304729, cg05956452, cg06261066, cg09157302, cg14608384, cg15289427, cg15608301, cg15707093, cg16266227, cg18869709, cg19470372, cg19864130, cg20686234, cg21913319, cg24720672, cg24747122, cg24983367, cg26584619, and cg27178401. In some instances, the methylation profile comprises twelve or more biomarkers selected from: cg01628067, cg03001333, cg04984818, cg05145233, cg05304729, cg05956452, cg06261066, cg09157302, cg14608384, cg15289427, cg15608301, cg15707093, cg16266227, cg18869709, cg19470372, cg19864130, cg20686234, cg21913319, cg24720672, cg24747122, cg24983367, cg26584619, and cg27178401. In some instances, the methylation profile comprises fifteen or more biomarkers selected from: cg01628067, cg03001333, cg04984818, cg05145233, cg05304729, cg05956452, cg06261066, cg09157302, cg14608384, cg15289427, cg15608301, cg15707093, cg16266227, cg18869709, cg19470372, cg19864130, cg20686234, cg21913319, cg24720672, cg24747122, cg24983367, cg26584619, and cg27178401. In some instances, the methylation profile comprises twenty or more biomarkers selected from: cg01628067, cg03001333, cg04984818, cg05145233, cg05304729, cg05956452, cg06261066, cg09157302, cg14608384, cg15289427, cg15608301, cg15707093, cg16266227, cg18869709, cg19470372, cg19864130, cg20686234, cg21913319, cg24720672, cg24747122, cg24983367, cg26584619, and cg27178401. In some instances, the methylation profile comprises cg01628067, cg03001333, cg04984818, cg05145233, cg05304729, cg05956452, cg06261066, cg09157302, cg14608384, cg15289427, cg15608301, cg15707093, cg16266227, cg18869709, cg19470372, cg19864130, cg20686234, cg21913319, cg24720672, cg24747122, cg24983367, cg26584619, and cg27178401.

Methylation Scores

In some instances, a methylation score is utilized to determine the prognosis of a subject. In some instances, prognosis refers to the prediction of the likelihood of cancer-attributable death or progression, including recurrence, metastatic spread, and drug resistance, of leukemia. The term "prediction" is used herein to refer to the likelihood that a subject will respond either favorably or unfavorably to a drug or set of drugs, and also the extent of those responses, or that a subject will survive, following chemotherapy for a certain period of time without cancer recurrence and/or following surgery (e.g., removal of the spleen). In some instances, a methylation score is utilized to determine the prognosis of a subject having AML or ALL.

In some embodiments, a methylation score of from about 1.5 to about 4 is associated with a "good" prognosis. In some instances, a "good" prognosis refers to the likelihood that a subject will likely respond favorably to a drug or set of drugs, leading to a complete or partial remission of leukemia or a decrease and/or a stop in the progression of leukemia. In some instances, a "good" prognosis refers to the survival of a subject of from at least 1 month to at least 90 years. In some instances, a "good" prognosis refers to the survival of a subject in which the survival of the subject upon treatment is from at least 1 month to at least 90 years. In some instances, the survival of a subject further refers to an extended survival rate of a subject receiving a treatment course relative to a subject without receiving the same course of treatment. In some cases, a "good" prognosis refers to an extended survival time of a subject receiving a treatment course relative to a subject without receiving the same course of treatment.

In some instances, a methylation score of from about 1.5 to about 4 is indicative of a survival from at least 1 month to at least 90 years. In some instances, a methylation score of from about 1.5 to about 4 is indicative of a survival of at least 2 months, 4 months, 6 months, 8 months, 10 months, 1 year, 1.5 years, 2 years, 3 years, 4 years, 5 years, 10 years, 15 years, 20 years, 30 years, 50 years, or more.

In some instances, a methylation score of from about 1.5 to about 3 is indicative of a survival from at least 1 month to at least 90 years. In some instances, a methylation score of from about 1.5 to about 3 is indicative of a survival of at least 2 months, 4 months, 6 months, 8 months, 10 months, 1 year, 1.5 years, 2 years, 3 years, 4 years, 5 years, 10 years, 15 years, 20 years, 30 years, 50 years, or more.

In some instances, a methylation score of from about 1.5 to about 2.5 is indicative of a survival from at least 1 month to at least 90 years. In some instances, a methylation score of from about 1.5 to about 2.5 is indicative of a survival of at least 2 months, 4 months, 6 months, 8 months, 10 months, 1 year, 1.5 years, 2 years, 3 years, 4 years, 5 years, 10 years, 15 years, 20 years, 30 years, 50 years, or more.

In some instances, a methylation score of from about 1.5 to about 2 is indicative of a survival from at least 1 month to at least 90 years. In some instances, a methylation score of from about 1.5 to about 2 is indicative of a survival of at least 2 months, 4 months, 6 months, 8 months, 10 months, 1 year, 1.5 years, 2 years, 3 years, 4 years, 5 years, 10 years, 15 years, 20 years, 30 years, 50 years, or more.

In some embodiments, a methylation score of from about 1.5 to about 4 is associated with a "good" prognosis in a subject having AML or ALL. In some embodiments, a methylation score of from about 1.5 to about 4, from about 1.5 to about 3.5, from about 1.5 to about 3, from about 1.5 to about 2.5, or from about 1.5 to about 2 is associated with a "good" prognosis in a subject having AML. In some embodiments, a methylation score of from about 1.5 to about 4, from about 1.5 to about 3.5, from about 1.5 to about 3, from about 1.5 to about 2.5, or from about 1.5 to about 2 is associated with a "good" prognosis in a subject having ALL.

In some instances, a methylation score of from about 1.5 to about 3 is indicative of a survival from at least 1 month to at least 90 years in a subject having AML or ALL. In some instances, a methylation score of from about 1.5 to about 3 is indicative of a survival of at least 2 months, 4 months, 6 months, 8 months, 10 months, 1 year, 1.5 years, 2 years, 3 years, 4 years, 5 years, 10 years, 15 years, 20 years, 30 years, 50 years, or more in a subject having AML or ALL. In some instances, a methylation score of from about 1.5 to about 3 is indicative of a survival for at least 2 months in a subject having AML or ALL. In some instances, a methylation score of from about 1.5 to about 3 is indicative of a survival for at least 3 months in a subject having AML or ALL. In some instances, a methylation score of from about 1.5 to about 3 is indicative of a survival for at least 4 months in a subject having AML or ALL. In some instances, a methylation score of from about 1.5 to about 3 is indicative of a survival for at least 5 months in a subject having AML or ALL. In some instances, a methylation score of from about 1.5 to about 3 is indicative of a survival for at least 6 months in a subject having AML or ALL. In some instances, a methylation score of from about 1.5 to about 3 is indicative of a survival for at least 8 months in a subject having AML or ALL. In some instances, a methylation score of from about 1.5 to about 3 is indicative of a survival for at least 10 months in a subject having AML or ALL. In some instances, a methylation score of from about 1.5 to about 3 is indicative of a survival for at least 1 year in a subject having AML or ALL. In some instances, a methylation score of from about 1.5 to about 3 is indicative of a survival for at least 1.5 years in a subject having AML or ALL. In some instances, a methylation score of from about 1.5 to about 3 is indicative of a survival for at least 2 years in a subject having AML or ALL. In some instances, a methylation score of from about 1.5 to about 3 is indicative of a survival for at least 2.5 years in a subject having AML or ALL. In some instances, a methylation score of from about 1.5 to about 3 is indicative of a survival for at least 3 years in a subject having AML or ALL. In some instances, a methylation score of from about 1.5 to about 3 is indicative of a survival for at least 4 years in a subject having AML or ALL. In some instances, a methylation score of from about 1.5 to about 3 is indicative of a survival for at least 5 years in a subject having AML or ALL.

In some instances, a methylation score of from about 1.5 to about 2.5 is indicative of a survival from at least 1 month to at least 90 years in a subject having AML or ALL. In some instances, a methylation score of from about 1.5 to about 2.5 is indicative of a survival of at least 2 months, 4 months, 6 months, 8 months, 10 months, 1 year, 1.5 years, 2 years, 3 years, 4 years, 5 years, 10 years, 15 years, 20 years, 30 years, 50 years, or more in a subject having AML or ALL. In some instances, a methylation score of from about 1.5 to about 2.5 is indicative of a survival for at least 2 months in a subject having AML or ALL. In some instances, a methylation score of from about 1.5 to about 2.5 is indicative of a survival for at least 3 months in a subject having AML or ALL. In some instances, a methylation score of from about 1.5 to about 2.5 is indicative of a survival for at least 4 months in a subject having AML or ALL. In some instances, a methylation score of from about 1.5 to about 2.5 is indicative of a survival for at least 5 months in a subject having AML or ALL. In some instances, a methylation score of from about 1.5 to about 2.5 is indicative of a survival for at least 6 months in a subject having AML or ALL. In some instances, a methylation score of from about 1.5 to about 2.5 is indicative of a survival for at least 8 months in a subject having AML or ALL. In some instances, a methylation score of from about 1.5 to about 2.5 is indicative of a survival for at least 10 months in a subject having AML or ALL. In some instances, a methylation score of from about 1.5 to about 2.5 is indicative of a survival for at least 1 year in a subject having AML or ALL. In some instances, a methylation score of from about 1.5 to about 2.5 is indicative of a survival for at least 1.5 years in a subject having AML or ALL. In some instances, a methylation score of from about 1.5 to about 2.5 is indicative of a survival for at least 2 years in a subject having AML or ALL. In some instances, a methylation score of from about 1.5 to about 2.5 is indicative of a survival for at least 2.5 years in a subject having AML or ALL. In some instances, a methylation score of from about 1.5 to about 2.5 is indicative of a survival for at least 3 years in a subject having AML or ALL. In some instances, a methylation score of from about 1.5 to about 2.5 is indicative of a survival for at least 4 years in a subject having AML or ALL. In some instances, a methylation score of from about 1.5 to about 2.5 is indicative of a survival for at least 5 years in a subject having AML or ALL.

In some instances, a methylation score of from about 1.5 to about 2 is indicative of a survival from at least 1 month to at least 90 years in a subject having AML or ALL. In some instances, a methylation score of from about 1.5 to about 2 is indicative of a survival of at least 2 months, 4 months, 6 months, 8 months, 10 months, 1 year, 1.5 years, 2 years, 3 years, 4 years, 5 years, 10 years, 15 years, 20 years, 30 years, 50 years, or more in a subject having AML or ALL. In some instances, a methylation score of from about 1.5 to about 2 is indicative of a survival for at least 2 months in a subject having AML or ALL. In some instances, a methylation score of from about 1.5 to about 2 is indicative of a survival for at least 3 months in a subject having AML or ALL. In some instances, a methylation score of from about 1.5 to about 2 is indicative of a survival for at least 4 months in a subject having AML or ALL. In some instances, a methylation score of from about 1.5 to about 2 is indicative of a survival for at least 5 months in a subject having AML or ALL. In some instances, a methylation score of from about 1.5 to about 2 is indicative of a survival for at least 6 months in a subject having AML or ALL. In some instances, a methylation score of from about 1.5 to about 2 is indicative of a survival for at least 8 months in a subject having AML or ALL. In some instances, a methylation score of from about 1.5 to about 2 is indicative of a survival for at least 10 months in a subject having AML or ALL.

In some instances, a methylation score of from about 1.5 to about 2 is indicative of a survival for at least 1 year in a subject having AML or ALL. In some instances, a methylation score of from about 1.5 to about 2 is indicative of a survival for at least 1.5 years in a subject having AML or ALL. In some instances, a methylation score of from about 1.5 to about 2 is indicative of a survival for at least 2 years in a subject having AML or ALL. In some instances, a methylation score of from about 1.5 to about 2 is indicative of a survival for at least 2.5 years in a subject having AML or ALL. In some instances, a methylation score of from about 1.5 to about 2 is indicative of a survival for at least 3 years in a subject having AML or ALL. In some instances, a methylation score of from about 1.5 to about 2 is indicative of a survival for at least 4 years in a subject having AML or ALL. In some instances, a methylation score of from about 1.5 to about 2 is indicative of a survival for at least 5 years in a subject having AML or ALL.

In some embodiments, a methylation score of less than about 1.5 is associated with a "poor" prognosis. In some instances, a "poor" prognosis refers to the likelihood that a subject will likely respond unfavorably to a drug or set of drugs, leading to a progression of leukemia (e.g., progression to metastatic leukemia) and/or to refractory of one or more therapeutic agents. In some instances, a "poor" prognosis refers to the likelihood that a subject will not respond to a drug or set of drugs, leading to a progression of leukemia. In some instances, a "poor" prognosis refers to the survival of a subject of from less than 5 years to less than 1 month. In some instances, a "poor" prognosis refers to the survival of a subject in which the survival of the subject upon treatment is from less than 5 years to less than 1 month. In some instances, a "poor" prognosis further refers to the likelihood that a subject will develop a refractory leukemia toward one or more drugs.

In some instances, a methylation score of less than 1.5 is indicative of a survival of from less than 5 years to less than 1 month. In some instances, a methylation score of less than 1.5 is indicative of a survival of less than 5 years, 4 years, 3 years, 2 years, 1.5 years, 1 year, 10 months, 8 months, 6 months, 4 months, or 2 months.

In some embodiments, a methylation score of less than about 1.5 is associated with a "poor" prognosis in a subject having AML or ALL. In some embodiments, a methylation score of less than about 1.5 is associated with a "poor" prognosis in a subject having AML. In some embodiments, a methylation score of less than about 1.5 is associated with a "poor" prognosis in a subject having ALL.

In some instances, a methylation score of less than 1.5 is indicative of a survival of from less than 5 years to less than 1 month in a subject having AML or ALL. In some instances, a methylation score of less than 1.5 is indicative of a survival of less than 5 years, 4 years, 3 years, 2 years, 1.5 years, 1 year, 10 months, 8 months, 6 months, 4 months, or 2 months in a subject having AML or ALL. In some instances, a methylation score of less than 1.5 is indicative of a survival of less than 5 years in a subject having AML or ALL. In some instances, a methylation score of less than 1.5 is indicative of a survival of less than 4 years in a subject having AML or ALL. In some instances, a methylation score of less than 1.5 is indicative of a survival of less than 3 years in a subject having AML or ALL. In some instances, a methylation score of less than 1.5 is indicative of a survival of less than 2.5 years in a subject having AML or ALL. In some instances, a methylation score of less than 1.5 is indicative of a survival of less than 2 years in a subject having AML or ALL. In some instances, a methylation score of less than 1.5 is indicative of a survival of less than 1.5 years in a subject having AML or ALL. In some instances, a methylation score of less than 1.5 is indicative of a survival of less than 1 year in a subject having AML or ALL. In some instances, a methylation score of less than 1.5 is indicative of a survival of less than 6 months in a subject having AML or ALL. In some instances, a methylation score of less than 1.5 is indicative of a survival of less than 5 months in a subject having AML or ALL. In some instances, a methylation score of less than 1.5 is indicative of a survival f of less than 4 months in a subject having AML or ALL. In some instances, a methylation score of less than 1.5 is indicative of a survival of less than 3 months in a subject having AML or ALL. In some instances, a methylation score of less than 1.5 is indicative of a survival of less than 2 months in a subject having AML or ALL. In some instances, a methylation score of less than 1.5 is indicative of a survival of less than 1 month in a subject having AML or ALL.

In some instances, one or more samples are obtained from a subject during the course of a treatment to monitor the progression of leukemia (e.g., acute myeloid leukemia or acute lymphoblastic leukemia) in the subject. In some instances, the subject initially has a methylation score of from about 1.5 to about 3 and progressively during each subsequent testing has a lower methylation score. For example, a subject initially has a methylation score of 3 and during subsequent testings, has methylation scores of 2.5, 2, 1.5, or 1. In such cases, the subject is further tested to determine the progression of leukemia (e.g., whether leukemia has progressed into a metastatic state or into a refractory state) and a treatment course is optionally altered based on the changes in prognosis.

In some embodiments, the methylation score is calculated based on model for a survival analysis. In some instances, a survival analysis is a statistic analysis for analyzing the expected duration of time until one or more events of interest happen. In some instances, survival analysis comprises Cox proportional hazards (PH) regression analysis, log-rank test or a product limit estimator. In some instances, the methylation score is calculated based on Cox proportional hazards (PH) regression analysis, log-rank test or product limit estimator. In some instances, the methylation score is calculated based on Cox proportional hazards (PH) regression analysis. In some embodiments, the methylation score is further calculated based on a log-rank test. In some instances, the log-rank test is a hypothesis test to compare the survival distribution of two samples (e.g., a training set and a validation set). In some instances, the log-rank test is also referred to as a Mantel-Cox test or a time-stratified Cochran-Mantel-Haenszel test. In some instances, the methylation score is additionally calculated based on a product limit estimator. A product limit estimator (also known as Kaplan-Meier estimator) is a non-parametric statistic used to estimate the survival function from lifetime data. In some embodiments, the methylation score is initially calculated based on Cox proportional hazards (PH) regression analysis and then reprocessed with a log-rank test.

Control

In some embodiments, a control is a methylation value, methylation level, or methylation profile of a sample. In some instances, the control comprises a set of methylation profiles, wherein each said methylation profile is generated from a biological sample obtained from a known cancer type. In some cases, the known cancer type is leukemia. In some cases, the known cancer type is a relapsed or refractory leukemia. In other cases, the known cancer type is a metastatic leukemia. In some cases, the known cancer type is acute lymphoblastic leukemia (ALL), acute myeloid leukemia (AML), chronic lymphocytic leukemia (CLL), chronic myeloid leukemia (CML), hairy cell leukemia (HCL), chronic myelomonocytic leukemia (CMML), juvenile myelomonocytic leukemia (JMML), large granular lymphocytic leukemia (LGL), or blastic plasmacytoid dendritic cell neoplasm (BPDCN).

Detection Methods

In some embodiments, a number of methods are utilized to measure, detect, determine, identify, and characterize the methylation status/level of a gene or a biomarker (e.g., CpG island-containing region/fragment) in identifying a subject as having leukemia, determining the leukemia subtype, the prognosis of a subject having leukemia, and the progression or regression of leukemia in subject in the presence of a therapeutic agent.

In some instances, the methylation profile is generated from a biological sample isolated from an individual. In some embodiments, the biological sample is a biopsy. In some instances, the biological sample is a tissue sample. In some instances, the biological sample is a tissue biopsy sample. In some instances, the biological sample is a blood sample. In other instances, the biological sample is a cell-free biological sample. In other instances, the biological sample is a circulating tumor DNA sample. In one embodiment, the biological sample is a cell-free biological sample containing circulating tumor DNA.

In some embodiments, a biomarker (or an epigenetic marker) is obtained from a liquid sample. In some embodiments, the liquid sample comprises blood and other liquid samples of biological origin (including, but not limited to, peripheral blood, sera, plasma, ascites, urine, cerebrospinal fluid (CSF), sputum, saliva, bone marrow, synovial fluid, aqueous humor, amniotic fluid, cerumen, breast milk, bronchoalveolar lavage fluid, semen, prostatic fluid, cowper's fluid or pre-ejaculatory fluid, female ejaculate, sweat, tears, cyst fluid, pleural and peritoneal fluid, pericardial fluid, ascites, lymph, chyme, chyle, bile, interstitial fluid, menses, pus, sebum, vomit, vaginal secretions/flushing, synovial fluid, mucosal secretion, stool water, pancreatic juice, lavage fluids from sinus cavities, bronchopulmonary aspirates, blastocyl cavity fluid, or umbilical cord blood). In some embodiments, the biological fluid is blood, a blood derivative or a blood fraction, e.g., serum or plasma. In a specific embodiment, a sample comprises a blood sample. In another embodiment, a serum sample is used. In another embodiment, a sample comprises urine. In some embodiments, the liquid sample also encompasses a sample that has been manipulated in any way after their procurement, such as by centrifugation, filtration, precipitation, dialysis, chromatography, treatment with reagents, washed, or enriched for certain cell populations.

In some embodiments, a biomarker (or an epigenetic marker) is obtained from a tissue sample. In some instances, a tissue corresponds to any cell(s). Different types of tissue correspond to different types of cells (e.g., liver, lung, blood, connective tissue, and the like), but also healthy cells vs. tumor cells or to tumor cells at various stages of neoplasia, or to displaced malignant tumor cells. In some embodiments, a tissue sample further encompasses a clinical sample, and also includes cells in culture, cell supernatants, organs, and the like. Samples also comprise fresh-frozen and/or formalin-fixed, paraffin-embedded tissue blocks, such as blocks prepared from clinical or pathological biopsies, prepared for pathological analysis or study by immunohistochemistry.

In some embodiments, a biomarker (or an epigenetic marker) is methylated or unmethylated in a normal sample (e.g., normal or control tissue without disease, or normal or control body fluid, stool, blood, serum, amniotic fluid), most importantly in healthy stool, blood, serum, amniotic fluid, or other body fluid. In other embodiments, a biomarker (or an epigenetic marker) is hypomethylated or hypermethylated in a sample from a patient having or at risk of a disease (e.g., one or more indications described herein); for example, at a decreased or increased (respectively) methylation frequency of at least about 50%, at least about 60%, at least about 70%, at least about 75%, at least about 80%, at least about 85%, at least about 90%, at least about 95%, or about 100% in comparison to a normal sample. In one embodiment, a sample is also hypomethylated or hypermethylated in comparison to a previously obtained sample analysis of the same patient having or at risk of a disease (e.g., one or more indications described herein), particularly to compare progression of a disease.

In some embodiments, a methylome comprises a set of epigenetic markers or biomarkers, such as a biomarker described above. In some instances, a methylome that corresponds to the methylome of a tumor of an organism (e.g., a human) is classified as a tumor methylome. In some cases, a tumor methylome is determined using tumor tissue or cell-free (or protein-free) tumor DNA in a biological sample. Other examples of methylomes of interest include the methylomes of organs that contribute DNA into a bodily fluid (e.g. methylomes of tissue such as brain, breast, lung, the prostrate and the kidneys, plasma, etc.).

In some embodiments, a plasma methylome is the methylome determined from the plasma or serum of an animal (e.g., a human). In some instances, the plasma methylome is an example of a cell-free or protein-free methylome since plasma and serum include cell-free DNA. The plasma methylome is also an example of a mixed methylome since it is a mixture of tumor and other methylomes of interest. In some instances, the urine methylome is determined from the urine sample of a subject. In some cases, a cellular methylome corresponds to the methylome determined from cells (e.g., blood cells) of the patient. The methylome of the blood cells is called the blood cell methylome (or blood methylome).

In some embodiments, DNA (e.g., genomic DNA such as extracted genomic DNA or treated genomic DNA) is isolated by any means standard in the art, including the use of commercially available kits. Briefly, wherein the DNA of interest is encapsulated in by a cellular membrane the biological sample is disrupted and lysed by enzymatic, chemical, or mechanical means. In some cases, the DNA solution is then cleared of proteins and other contaminants e.g. by digestion with proteinase K. The DNA is then recovered from the solution. In such cases, this is carried out by means of a variety of methods including salting out, organic extraction, or binding of the DNA to a solid phase support. In some instances, the choice of method is affected by several factors including time, expense, and required quantity of DNA.

Wherein the sample DNA is not enclosed in a membrane (e.g. circulating DNA from a cell free sample such as blood or urine) methods standard in the art for the isolation and/or purification of DNA are optionally employed (See, for example, Bettegowda et al. Detection of Circulating Tumor DNA in Early- and Late-Stage Human Malignancies. Sci. Transl. Med, 6(224): ra24. 2014). Such methods include the use of a protein degenerating reagent e.g. chaotropic salt e.g. guanidine hydrochloride or urea; or a detergent e.g. sodium dodecyl sulphate (SDS), cyanogen bromide. Alternative methods include, but are not limited to, ethanol precipitation or propanol precipitation, or vacuum concentration amongst others by means of a centrifuge. In some cases, the person skilled in the art also make use of devices such as filter devices e.g. ultrafiltration, silica surfaces or membranes, magnetic particles, polystyrol particles, polystyrol surfaces, positively charged surfaces, and positively charged membranes, charged membranes, charged surfaces, charged switch membranes, charged switched surfaces.

In some instances, once the nucleic acids have been extracted, methylation analysis is carried out by any means known in the art. A variety of methylation analysis procedures are known in the art and in some cases are used to practice the methods disclosed herein. These assays allow for determination of the methylation state of one or a plurality of CpG sites within a tissue sample. In addition, these methods may be used for absolute or relative quantification of methylated nucleic acids. Such methylation assays involve, among other techniques, two major steps. The first step is a methylation specific reaction or separation, such as (i) bisulfite treatment, (ii) methylation specific binding, or (iii) methylation specific restriction enzymes.

The second major step involves (i) amplification and detection, or (ii) direct detection, by a variety of methods such as (a) PCR (sequence-specific amplification) such as Taqman®, (b) DNA sequencing of untreated and bisulfite-treated DNA, (c) sequencing by ligation of dye-modified probes (including cyclic ligation and cleavage), (d) pyrosequencing, (e) single-molecule sequencing, (f) mass spectroscopy, or (g) Southern blot analysis.

Additionally, restriction enzyme digestion of PCR products amplified from bisulfite-converted DNA may be used, e.g., the method described by Sadri and Hornsby (1996, Nucl. Acids Res. 24:5058-5059), or COBRA (Combined Bisulfite Restriction Analysis) (Xiong and Laird, 1997, Nucleic Acids Res. 25:2532-2534). COBRA analysis is a quantitative methylation assay useful for determining DNA methylation levels at specific gene loci in small amounts of genomic DNA. Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Frommer et al, 1992, Proc. Nat. Acad. Sci. USA, 89, 1827-1831). PCR amplification of the bisulfite converted DNA is then performed using primers specific for the CpG sites of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from micro-dissected paraffin-embedded tissue samples. Typical reagents (e.g., as might be found in a typical COBRA-based kit) for COBRA analysis may include, but are not limited to: PCR primers for specific gene (or methylation-altered DNA sequence or CpG island); restriction enzyme and appropriate buffer; gene-hybridization oligo; control hybridization oligo; kinase labeling kit for oligo probe; and radioactive nucleotides. Additionally, bisulfite conversion reagents may include: DNA denaturation buffer; sulfo nation buffer; DNA recovery reagents or kits (e.g., precipitation, ultrafiltration, affinity column); desulfonation buffer; and DNA recovery components.

In an embodiment, the methylation profile of selected CpG sites is determined using methylation-Specific PCR (MSP). MSP allows for assessing the methylation status of virtually any group of CpG sites within a CpG island, independent of the use of methylation-sensitive restriction enzymes (Herman et al, 1996, Proc. Nat. Acad. Sci. USA, 93, 9821-9826; U.S. Pat. Nos. 5,786,146, 6,017,704, 6,200, 756, 6,265,171 (Herman and Baylin); U.S. Pat. Pub. No. 2010/0144836 (Van Engeland et al)). Briefly, DNA is modified by a deaminating agent such as sodium bisulfite to convert unmethylated, but not methylated cytosines to uracil, and subsequently amplified with primers specific for methylated versus unmethylated DNA. In some instances, typical reagents (e.g., as might be found in a typical MSP-based kit) for MSP analysis include, but are not limited to: methylated and unmethylated PCR primers for specific gene (or methylation-altered DNA sequence or CpG island), optimized PCR buffers and deoxynucleotides, and specific probes. The ColoSure™ test is a commercially available test for colon cancer based on the MSP technology and measurement of methylation of the vimentin gene (Itzkowitz et al, 2007, Clin Gastroenterol. Hepatol. 5(1), 111-117). Alternatively, one may use quantitative multiplexed methylation specific PCR (QM-PCR), as described by Fackler et al. Fackler et al, 2004, Cancer Res. 64(13) 4442-4452; or Fackler et al, 2006, Clin. Cancer Res. 12(11 Pt 1) 3306-3310.

In an embodiment, the methylation profile of selected CpG sites is determined using MethyLight and/or Heavy Methyl Methods. The MethyLight and Heavy Methyl assays are a high-throughput quantitative methylation assay that utilizes fluorescence-based real-time PCR (Taq Man®) technology that requires no further manipulations after the PCR step (Eads, C. A. et al, 2000, Nucleic Acid Res. 28, e 32; Cottrell et al, 2007, J. Urology 177, 1753, U.S. Pat. No. 6,331,393 (Laird et al)). Briefly, the MethyLight process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed either in an "unbiased" (with primers that do not overlap known CpG methylation sites) PCR reaction, or in a "biased" (with PCR primers that overlap known CpG dinucleotides) reaction. In some cases, sequence discrimination occurs either at the level of the amplification process or at the level of the fluorescence detection process, or both. In some cases, the MethyLight assay is used as a quantitative test for methylation patterns in the genomic DNA sample, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the "MSP" technique), or with oligonucleotides covering potential methylation sites. Typical reagents (e.g., as might be found in a typical MethyLight-based kit) for MethyLight analysis may include, but are not limited to: PCR primers for specific gene (or methylation-altered DNA sequence or CpG island); TaqMan® probes; optimized PCR buffers and deoxynucleotides; and Taq polymerase. The MethyLight technology is used for the commercially available tests for lung cancer (epi proLung BL Reflex Assay); colon cancer (epi proColon assay and mSEPT9 assay) (Epigenomics, Berlin, Germany) PCT Pub. No. WO 2003/064701 (Schweikhardt and Sledziewski).

Quantitative MethyLight uses bisulfite to convert genomic DNA and the methylated sites are amplified using PCR with methylation independent primers. Detection probes specific for the methylated and unmethylated sites with two different fluorophores provides simultaneous quantitative measurement of the methylation. The Heavy Methyl technique begins with bisulfate conversion of DNA. Next specific blockers prevent the amplification of unmethylated DNA. Methylated genomic DNA does not bind the blockers and their sequences will be amplified. The amplified sequences are detected with a methylation specific probe. (Cottrell et al, 2004, Nuc. Acids Res. 32:e10).

The Ms-SNuPE technique is a quantitative method for assessing methylation differences at specific CpG sites based on bisulfite treatment of DNA, followed by single-nucleotide primer extension (Gonzalgo and Jones, 1997, Nucleic Acids Res. 25, 2529-2531). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. In some cases, small amounts of DNA are analyzed (e.g., microdissected pathology sections), and the method avoids utilization of restriction enzymes for determining the methylation status at CpG sites. Typical reagents (e.g., as is found in a typical Ms-SNuPE-based kit) for Ms-SNuPE analysis include, but are not limited to: PCR primers for specific gene (or methylation-altered DNA sequence or CpG island); optimized PCR buffers and deoxynucleotides; gel extraction kit; positive control primers; Ms-SNuPE primers for specific gene; reaction buffer (for the Ms-SNuPE reaction); and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

In another embodiment, the methylation status of selected CpG sites is determined using differential Binding-based Methylation Detection Methods. For identification of differentially methylated regions, one approach is to capture methylated DNA. This approach uses a protein, in which the methyl binding domain of MBD2 is fused to the Fc fragment of an antibody (MBD-FC) (Gebhard et al, 2006, Cancer Res. 66:6118-6128; and PCT Pub. No. WO 2006/056480 A2 (Relhi)). This fusion protein has several advantages over conventional methylation specific antibodies. The MBD FC has a higher affinity to methylated DNA and it binds double stranded DNA. Most importantly the two proteins differ in the way they bind DNA. Methylation specific antibodies bind DNA stochastically, which means that only a binary answer can be obtained. The methyl binding domain of MBD-FC, on the other hand, binds DNA molecules regardless of their methylation status. The strength of this protein-DNA interaction is defined by the level of DNA methylation. After binding genomic DNA, eluate solutions of increasing salt concentrations can be used to fractionate non-methylated and methylated DNA allowing for a more controlled separation (Gebhard et al, 2006, Nucleic Acids Res. 34: e82). Consequently this method, called Methyl-CpG immunoprecipitation (MCIP), not only enriches, but also fractionates genomic DNA according to methylation level, which is particularly helpful when the unmethylated DNA fraction should be investigated as well.

In an alternative embodiment, a 5-methyl cytidine antibody to bind and precipitate methylated DNA. Antibodies are available from Abcam (Cambridge, Mass.), Diagenode (Sparta, N.J.) or Eurogentec (c/o AnaSpec, Fremont, Calif.). Once the methylated fragments have been separated they may be sequenced using microarray based techniques such as methylated CpG-island recovery assay (MIRA) or methylated DNA immunoprecipitation (MeDIP) (Pelizzola et al, 2008, Genome Res. 18, 1652-1659; O'Geen et al, 2006, BioTechniques 41(5), 577-580, Weber et al, 2005, Nat. Genet. 37, 853-862; Horak and Snyder, 2002, Methods Enzymol, 350, 469-83; Lieb, 2003, Methods Mol Biol, 224, 99-109). Another technique is methyl-CpG binding domain column/segregation of partly melted molecules (MBD/SPM, Shiraishi et al, 1999, Proc. Natl. Acad. Sci. USA 96(6):2913-2918).

In some embodiments, methods for detecting methylation include randomly shearing or randomly fragmenting the genomic DNA, cutting the DNA with a methylation-dependent or methylation-sensitive restriction enzyme and subsequently selectively identifying and/or analyzing the cut or uncut DNA. Selective identification can include, for example, separating cut and uncut DNA (e.g., by size) and quantifying a sequence of interest that was cut or, alternatively, that was not cut. See, e.g., U.S. Pat. No. 7,186,512. Alternatively, the method can encompass amplifying intact DNA after restriction enzyme digestion, thereby only amplifying DNA that was not cleaved by the restriction enzyme in the area amplified. See, e.g., U.S. Pat. No. 7,910,296; U.S. Pat. No. 7,901,880; and U.S. Pat. No. 7,459,274. In some embodiments, amplification can be performed using primers that are gene specific.

For example, there are methyl-sensitive enzymes that preferentially or substantially cleave or digest at their DNA recognition sequence if it is non-methylated. Thus, an unmethylated DNA sample is cut into smaller fragments than a methylated DNA sample. Similarly, a hypermethylated DNA sample is not cleaved. In contrast, there are methyl-sensitive enzymes that cleave at their DNA recognition sequence only if it is methylated. Methyl-sensitive enzymes that digest unmethylated DNA suitable for use in methods of the technology include, but are not limited to, HpaII, HhaI, MaeII, BstUI and AciI. In some instances, an enzyme that is used is HpaII that cuts only the unmethylated sequence CCGG. In other instances, another enzyme that is used is HhaI that cuts only the unmethylated sequence GCGC. Both enzymes are available from New England BioLabs®, Inc. Combinations of two or more methyl-sensitive enzymes that digest only unmethylated DNA are also used. Suitable enzymes that digest only methylated DNA include, but are not limited to, DpnI, which only cuts at fully methylated 5'-GATC sequences, and McrBC, an endonuclease, which cuts DNA containing modified cytosines (5-methylcytosine or 5-hydroxymethylcytosine or N4-methylcytosine) and cuts at recognition site 5' . . . PumC(N4o-3ooo) PumC . . . 3' (New England BioLabs, Inc., Beverly, Mass.). Cleavage methods and procedures for selected restriction enzymes for cutting DNA at specific sites are well known to the skilled artisan. For example, many suppliers of restriction enzymes provide information on conditions and types of DNA sequences cut by specific restriction enzymes, including New England BioLabs, Pro-Mega Biochems, Boehringer-Mannheim, and the like. Sambrook et al. (See Sambrook et al. Molecular Biology: A Laboratory Approach, Cold Spring Harbor, N.Y. 1989) provide a general description of methods for using restriction enzymes and other enzymes.

In some instances, a methylation-dependent restriction enzyme is a restriction enzyme that cleaves or digests DNA at or in proximity to a methylated recognition sequence, but does not cleave DNA at or near the same sequence when the recognition sequence is not methylated. Methylation-dependent restriction enzymes include those that cut at a methylated recognition sequence (e.g., DpnI) and enzymes that cut at a sequence near but not at the recognition sequence (e.g., McrBC). For example, McrBC's recognition sequence is 5' RmC (N40-3000) RmC 3' where "R" is a purine and "mC" is a methylated cytosine and "N40-3000" indicates the distance between the two RmC half sites for which a restriction event has been observed. McrBC generally cuts close to one half-site or the other, but cleavage positions are typically distributed over several base pairs, approximately 30 base pairs from the methylated base. McrBC sometimes cuts 3' of both half sites, sometimes 5' of both half sites, and sometimes between the two sites. Exemplary methylation-dependent restriction enzymes include, e.g., McrBC, McrA, MrrA, BisI, GlaI and DpnI. One of skill in the art will appreciate that any methylation-dependent restriction enzyme, including homologs and orthologs of the restriction enzymes described herein, is also suitable for use with one or more methods described herein.

In some cases, a methylation-sensitive restriction enzyme is a restriction enzyme that cleaves DNA at or in proximity to an unmethylated recognition sequence but does not cleave at or in proximity to the same sequence when the recognition sequence is methylated. Exemplary methylation-sensitive restriction enzymes are described in, e.g., McClelland et al, 22(17) NUCLEIC ACIDS RES. 3640-59 (1994). Suitable methylation-sensitive restriction enzymes that do not cleave DNA at or near their recognition sequence when a cytosine within the recognition sequence is methylated at position C5 include, e.g., Aat II, Aci I, Acd I, Age I, Alu I, Asc I, Ase I, AsiS I, Bbe I, BsaA I, BsaH I, BsiE I, BsiW I, BsrF I, BssH II, BssK I, BstB I, BstN I, BstU I, Cla I, Eae I, Eag I, Fau I, Fse I, Hha I, HinPl I, HinC II, Hpa II, Hpy99 I, HpyCH4 IV, Kas I, Mbo I, Mlu I, MapAl I, Msp I, Nae I, Nar I, Not I, Pml I, Pst I, Pvu I, Rsr II, Sac II, Sap I, Sau3A I, Sfl I, Sfo I, SgrA I, Sma I, SnaB I, Tsc I, Xma I, and Zra I. Suitable methylation-sensitive restriction enzymes that do not cleave DNA at or near their recognition sequence when an adenosine within the recognition sequence is methylated at position N6 include, e.g., Mbo I. One of skill in the art will appreciate that any methylation-sensitive restriction enzyme, including homologs and orthologs of the restriction enzymes described herein, is also suitable for use with one or more of the methods described herein. One of skill in the art will further appreciate that a methylation-sensitive restriction enzyme that fails to cut in the presence of methylation of a cytosine at or near its recognition sequence may be insensitive to the presence of methylation of an adenosine at or near its recognition sequence. Likewise, a methylation-sensitive restriction enzyme that fails to cut in the presence of methylation of an adenosine at or near its recognition sequence may be insensitive to the presence of methylation of a cytosine at or near its recognition sequence. For example, Sau3AI is sensitive (i.e., fails to cut) to the presence of a methylated cytosine at or near its recognition sequence, but is insensitive (i.e., cuts) to the presence of a methylated adenosine at or near its recognition sequence. One of skill in the art will also appreciate that some methylation-sensitive restriction enzymes are blocked by methylation of bases on one or both strands of DNA encompassing of their recognition sequence, while other methylation-sensitive restriction enzymes are blocked only by methylation on both strands, but can cut if a recognition site is hemi-methylated.

In alternative embodiments, adaptors are optionally added to the ends of the randomly fragmented DNA, the DNA is then digested with a methylation-dependent or methylation-sensitive restriction enzyme, and intact DNA is subsequently amplified using primers that hybridize to the adaptor sequences. In this case, a second step is performed to determine the presence, absence or quantity of a particular gene in an amplified pool of DNA. In some embodiments, the DNA is amplified using real-time, quantitative PCR.

In other embodiments, the methods comprise quantifying the average methylation density in a target sequence within a population of genomic DNA. In some embodiments, the method comprises contacting genomic DNA with a methylation-dependent restriction enzyme or methylation-sensitive restriction enzyme under conditions that allow for at least some copies of potential restriction enzyme cleavage sites in the locus to remain uncleaved; quantifying intact copies of the locus; and comparing the quantity of amplified product to a control value representing the quantity of methylation of control DNA, thereby quantifying the average methylation density in the locus compared to the methylation density of the control DNA.

In some instances, the quantity of methylation of a locus of DNA is determined by providing a sample of genomic DNA comprising the locus, cleaving the DNA with a restriction enzyme that is either methylation-sensitive or methylation-dependent, and then quantifying the amount of intact DNA or quantifying the amount of cut DNA at the DNA locus of interest. The amount of intact or cut DNA will depend on the initial amount of genomic DNA containing the locus, the amount of methylation in the locus, and the number (i.e., the fraction) of nucleotides in the locus that are methylated in the genomic DNA. The amount of methylation in a DNA locus can be determined by comparing the quantity of intact DNA or cut DNA to a control value representing the quantity of intact DNA or cut DNA in a similarly-treated DNA sample. The control value can represent a known or predicted number of methylated nucleotides. Alternatively, the control value can represent the quantity of intact or cut DNA from the same locus in another (e.g., normal, non-diseased) cell or a second locus.

By using at least one methylation-sensitive or methylation-dependent restriction enzyme under conditions that allow for at least some copies of potential restriction enzyme cleavage sites in the locus to remain uncleaved and subsequently quantifying the remaining intact copies and comparing the quantity to a control, average methylation density of a locus can be determined. If the methylation-sensitive restriction enzyme is contacted to copies of a DNA locus under conditions that allow for at least some copies of potential restriction enzyme cleavage sites in the locus to remain uncleaved, then the remaining intact DNA will be directly proportional to the methylation density, and thus may be compared to a control to determine the relative methylation density of the locus in the sample. Similarly, if a methylation-dependent restriction enzyme is contacted to copies of a DNA locus under conditions that allow for at least some copies of potential restriction enzyme cleavage sites in the locus to remain uncleaved, then the remaining intact DNA will be inversely proportional to the methylation density, and thus may be compared to a control to determine the relative methylation density of the locus in the sample. Such assays are disclosed in, e.g., U.S. Pat. No. 7,910,296.

The methylated CpG island amplification (MCA) technique is a method that can be used to screen for altered methylation patterns in genomic DNA, and to isolate specific sequences associated with these changes (Toyota et al, 1999, Cancer Res. 59, 2307-2312, U.S. Pat. No. 7,700,324 (Issa et al)). Briefly, restriction enzymes with different sensitivities to cytosine methylation in their recognition sites are used to digest genomic DNAs from primary tumors, cell lines, and normal tissues prior to arbitrarily primed PCR amplification. Fragments that show differential methylation are cloned and sequenced after resolving the PCR products on high-resolution polyacrylamide gels. The cloned fragments are then used as probes for Southern analysis to confirm differential methylation of these regions. Typical reagents (e.g., as might be found in a typical MCA-based kit) for MCA analysis may include, but are not limited to: PCR primers for arbitrary priming Genomic DNA; PCR buffers and nucleotides, restriction enzymes and appropriate buffers; gene-hybridization oligos or probes; control hybridization oligos or probes.

Additional methylation detection methods include those methods described in, e.g., U.S. Pat. No. 7,553,627; U.S. Pat. No. 6,331,393; U.S. patent Ser. No. 12/476,981; U.S. Patent Publication No. 2005/0069879; Rein, et al, 26(10) NUCLEIC ACIDS RES. 2255-64 (1998); and Olek et al, 17(3) NAT. GENET. 275-6 (1997).

In another embodiment, the methylation status of selected CpG sites is determined using Methylation-Sensitive High Resolution Melting (HRM). Recently, Wojdacz et al. reported methylation-sensitive high resolution melting as a technique to assess methylation. (Wojdacz and Dobrovic, 2007, Nuc. Acids Res. 35(6) e41; Wojdacz et al. 2008, Nat. Prot. 3(12) 1903-1908; Balic et al, 2009 J. Mol. Diagn. 11 102-108; and US Pat. Pub. No. 2009/0155791 (Wojdacz et al)). A variety of commercially available real time PCR machines have HRM systems including the Roche LightCycler480, Corbett Research RotorGene6000, and the Applied Biosystems 7500. HRM may also be combined with other amplification techniques such as pyrosequencing as described by Candiloro et al. (Candiloro et al, 2011, Epigenetics 6(4) 500-507).

In another embodiment, the methylation status of selected CpG locus is determined using a primer extension assay, including an optimized PCR amplification reaction that produces amplified targets for analysis using mass spectrometry. The assay can also be done in multiplex. Mass spectrometry is a particularly effective method for the detection of polynucleotides associated with the differentially methylated regulatory elements. The presence of the polynucleotide sequence is verified by comparing the mass of the detected signal with the expected mass of the polynucleotide of interest. The relative signal strength, e.g., mass peak on a spectra, for a particular polynucleotide sequence indicates the relative population of a specific allele, thus enabling calculation of the allele ratio directly from the data. This method is described in detail in PCT Pub. No. WO 2005/012578A1 (Beaulieu et al). For methylation analysis, the assay can be adopted to detect bisulfite introduced methylation dependent C to T sequence changes. These methods are particularly useful for performing multiplexed amplification reactions and multiplexed primer extension reactions (e.g., multiplexed homogeneous primer mass extension (hME) assays) in a single well to further increase the throughput and reduce the cost per reaction for primer extension reactions.

Other methods for DNA methylation analysis include restriction landmark genomic scanning (RLGS, Costello et al, 2002, Meth. Mol Biol, 200, 53-70), methylation-sensitive-representational difference analysis (MS-RDA, Ushijima and Yamashita, 2009, Methods Mol Biol 507, 117-130). Comprehensive high-throughput arrays for relative methylation (CHARM) techniques are described in WO 2009/021141 (Feinberg and Irizarry). The Roche® NimbleGen® microarrays including the Chromatin Immunoprecipitation-on-chip (ChIP-chip) or methylated DNA immunoprecipitation-on-chip (MeDIP-chip). These tools have been used for a variety of cancer applications including melanoma, liver cancer and lung cancer (Koga et al, 2009, Genome Res., 19, 1462-1470; Acevedo et al, 2008, Cancer Res., 68, 2641-2651; Rauch et al, 2008, Proc. Nat. Acad. Sci. USA, 105, 252-257). Others have reported bisulfate conversion, padlock probe hybridization, circularization, amplification and next generation or multiplexed sequencing for high throughput detection of methylation (Deng et al, 2009, Nat. Biotechnol 27, 353-360; Ball et al, 2009, Nat. Biotechnol 27, 361-368; U.S. Pat. No. 7,611,869 (Fan)). As an alternative to bisulfate oxidation, Bayeyt et al. have reported selective oxidants that oxidize 5-methylcytosine, without reacting with thymidine, which are followed by PCR or pyro sequencing (WO 2009/049916 (Bayeyt et al).

In some instances, quantitative amplification methods (e.g., quantitative PCR or quantitative linear amplification) are used to quantify the amount of intact DNA within a locus flanked by amplification primers following restriction digestion. Methods of quantitative amplification are disclosed in, e.g., U.S. Pat. No. 6,180,349; U.S. Pat. No. 6,033,854; and U.S. Pat. No. 5,972,602, as well as in, e.g., DeGraves, et al, 34(1) BIOTECHNIQUES 106-15 (2003); Deiman B, et al., 20(2) MOL. BIOTECHNOL. 163-79 (2002); and Gibson et al, 6 GENOME RESEARCH 995-1001 (1996).

Following reaction or separation of nucleic acid in a methylation specific manner, the nucleic acid in some cases are subjected to sequence-based analysis. For example, once it is determined that one particular genomic sequence from a sample is hypermethylated or hypomethylated compared to its counterpart, the amount of this genomic sequence can be determined. Subsequently, this amount can be compared to a standard control value and used to determine the present of leukemia in the sample. In many instances, it is desirable to amplify a nucleic acid sequence using any of several nucleic acid amplification procedures which are well known in the art. Specifically, nucleic acid amplification is the chemical or enzymatic synthesis of nucleic acid copies which contain a sequence that is complementary to a nucleic acid sequence being amplified (template). The methods and kits may use any nucleic acid amplification or detection methods known to one skilled in the art, such as those described in U.S. Pat. No. 5,525,462 (Takarada et al); U.S. Pat. No. 6,114,117 (Hepp et al); U.S. Pat. No. 6,127,120 (Graham et al); U.S. Pat. No. 6,344,317 (Urnovitz); U.S. Pat. No. 6,448,001 (Oku); U.S. Pat. No. 6,528,632 (Catanzariti et al); and PCT Pub. No. WO 2005/111209 (Nakajima et al).

In some embodiments, the nucleic acids are amplified by PCR amplification using methodologies known to one skilled in the art. One skilled in the art will recognize, however, that amplification can be accomplished by any known method, such as ligase chain reaction (LCR), Q-replicas amplification, rolling circle amplification, transcription amplification, self-sustained sequence replication, nucleic acid sequence-based amplification (NASBA), each of which provides sufficient amplification. Branched-DNA technology is also optionally used to qualitatively demonstrate the presence of a sequence of the technology, which represents a particular methylation pattern, or to quantitatively determine the amount of this particular genomic sequence in a sample. Nolte reviews branched-DNA signal amplification for direct quantitation of nucleic acid sequences in clinical samples (Nolte, 1998, Adv. Clin. Chem. 33:201-235).

The PCR process is well known in the art and include, for example, reverse transcription PCR, ligation mediated PCR, digital PCR (dPCR), or droplet digital PCR (ddPCR). For a review of PCR methods and protocols, see, e.g., Innis et al, eds., PCR Protocols, A Guide to Methods and Application, Academic Press, Inc., San Diego, Calif. 1990; U.S. Pat. No. 4,683,202 (Mullis). PCR reagents and protocols are also available from commercial vendors, such as Roche Molecular Systems. In some instances, PCR is carried out as an automated process with a thermostable enzyme. In this process, the temperature of the reaction mixture is cycled through a denaturing region, a primer annealing region, and an extension reaction region automatically. Machines specifically adapted for this purpose are commercially available.

In some embodiments, amplified sequences are also measured using invasive cleavage reactions such as the Invader® technology (Zou et al, 2010, Association of Clinical Chemistry (AACC) poster presentation on Jul. 28, 2010, "Sensitive Quantification of Methylated Markers with a Novel Methylation Specific Technology; and U.S. Pat. No. 7,011,944 (Prudent et al)).

Suitable next generation sequencing technologies are widely available. Examples include the 454 Life Sciences platform (Roche, Branford, Conn.) (Margulies et al. 2005 Nature, 437, 376-380); Illumina's Genome Analyzer, GoldenGate Methylation Assay, or Infinium Methylation Assays, i.e., Infinium HumanMethylation 27K BeadArray or VeraCode GoldenGate methylation array (Illumina, San Diego, Calif.; Bibkova et al, 2006, Genome Res. 16, 383-393; U.S. Pat. Nos. 6,306,597 and 7,598,035 (Macevicz); U.S. Pat. No. 7,232,656 (Balasubramanian et al.)); QX200™ Droplet Digital™ PCR System from Bio-Rad; or DNA Sequencing by Ligation, SOLiD System (Applied Biosystems/Life Technologies; U.S. Pat. Nos. 6,797,470, 7,083,917, 7,166,434, 7,320,865, 7,332,285, 7,364,858, and 7,429,453 (Barany et al); the Helicos True Single Molecule DNA sequencing technology (Harris et al, 2008 Science, 320, 106-109; U.S. Pat. Nos. 7,037,687 and 7,645,596 (Williams et al); U.S. Pat. No. 7,169,560 (Lapidus et al); U.S. Pat. No. 7,769,400 (Harris)), the single molecule, real-time (SMRT™) technology of Pacific Biosciences, and sequencing (Soni and Meller, 2007, Clin. Chem. 53, 1996-2001); semiconductor sequencing (Ion Torrent; Personal Genome Machine); DNA nanoball sequencing; sequencing using technology from Dover Systems (Polonator), and technologies that do not require amplification or otherwise transform native DNA prior to sequencing (e.g., Pacific Biosciences and Helicos), such as nanopore-based strategies (e.g., Oxford Nanopore, Genia Technologies, and Nabsys). These systems allow the sequencing of many nucleic acid molecules isolated from a specimen at high orders of multiplexing in a parallel fashion. Each of these platforms allow sequencing of clonally expanded or non-amplified single molecules of nucleic acid fragments. Certain platforms involve, for example, (i) sequencing by ligation of dye-modified probes (including cyclic ligation and cleavage), (ii) pyrosequencing, and (iii) single-molecule sequencing.

Pyrosequencing is a nucleic acid sequencing method based on sequencing by synthesis, which relies on detection of a pyrophosphate released on nucleotide incorporation. Generally, sequencing by synthesis involves synthesizing, one nucleotide at a time, a DNA strand complimentary to the strand whose sequence is being sought. Study nucleic acids may be immobilized to a solid support, hybridized with a sequencing primer, incubated with DNA polymerase, ATP sulfurylase, luciferase, apyrase, adenosine 5' phosphsulfate and luciferin. Nucleotide solutions are sequentially added and removed. Correct incorporation of a nucleotide releases a pyrophosphate, which interacts with ATP sulfurylase and produces ATP in the presence of adenosine 5' phosphsulfate, fueling the luciferin reaction, which produces a chemiluminescent signal allowing sequence determination. Machines for pyrosequencing and methylation specific reagents are available from Qiagen, Inc. (Valencia, Calif.). See also Tost and Gut, 2007, Nat. Prot. 2 2265-2275. An example of a system that can be used by a person of ordinary skill based on pyrosequencing generally involves the following steps: ligating an adaptor nucleic acid to a study nucleic acid and hybridizing the study nucleic acid to a bead; amplifying a nucleotide sequence in the study nucleic acid in an emulsion; sorting beads using a picoliter multiwell solid support; and sequencing amplified nucleotide sequences by pyrosequencing methodology (e.g., Nakano et al, 2003, J. Biotech. 102, 117-124). Such a system can be used to exponentially amplify amplification products generated by a process described herein, e.g., by ligating a heterologous nucleic acid to the first amplification product generated by a process described herein.

CpG Methylation Data Analysis Methods

In certain embodiments, the methylation values measured for biomarkers of a biomarker panel are mathematically combined and the combined value is correlated to the underlying diagnostic question. In some instances, methylated biomarker values are combined by any appropriate state of the art mathematical method. Well-known mathematical methods for correlating a biomarker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate an epigenetic marker or biomarker combination described herein. In one embodiment, the method used in a correlating methylation status of an epigenetic marker or biomarker combination, e.g. to diagnose leukemia or a leukemia subtype, is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 J. OF COMPUTATIONAL AND GRAPHICAL STATISTICS 475-511 (2003); Friedman, J. H., 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 MACHINE LEARNING 5-32 (2001); Pepe, M. S., The Statistical Evaluation of Medical Tests for Classification and Prediction, Oxford Statistical Science Series, 28 (2003); and Duda, R. O., Hart, P. E., Stork, D. O., Pattern Classification, Wiley Interscience, 2nd Edition (2001).

In one embodiment, the correlated results for each methylation panel are rated by their correlation to the disease or tumor type positive state, such as for example, by p-value test or t-value test or F-test. Rated (best first, i.e. low p- or t-value) biomarkers are then subsequently selected and added to the methylation panel until a certain diagnostic value is reached. Such methods include identification of methylation panels, or more broadly, genes that were differentially methylated among several classes using, for example, a random-variance t-test (Wright G. W. and Simon R, Bioinformatics 19:2448-2455, 2003). Other methods include the step of specifying a significance level to be used for determining the epigenetic markers that will be included in the biomarker panel. Epigenetic markers that are differentially methylated between the classes at a univariate parametric significance level less than the specified threshold are included in the panel. It doesn't matter whether the specified significance level is small enough to exclude enough false discoveries. In some problems better prediction is achieved by being more liberal about the biomarker panels used as features. In some cases, the panels are biologically interpretable and clinically applicable, however, if fewer markers are included. Similar to cross-validation, biomarker selection is repeated for each training set created in the cross-validation process. That is for the purpose of providing an unbiased estimate of prediction error. The methylation panel for use with new patient sample data is the one resulting from application of the methylation selection and classifier of the "known" methylation information, or control methylation panel.

Models for utilizing methylation profile to predict the class of future samples can also be used. These models may be based on the Compound Covariate Predictor (Radmacher et al. Journal of Computational Biology 9:505-511, 2002), Diagonal Linear Discriminant Analysis (Dudoit et al. Journal of the American Statistical Association 97:77-87, 2002), Nearest Neighbor Classification (also Dudoit et al.), and Support Vector Machines with linear kernel (Ramaswamy et al. PNAS USA 98:15149-54, 2001). The models incorporated markers that were differentially methylated at a given significance level (e.g. 0.01, 0.05 or 0.1) as assessed by the random variance t-test (Wright G. W. and Simon R. Bioinformatics 19:2448-2455, 2003). The prediction error of each model using cross validation, preferably leave-one-out cross-validation (Simon et al. Journal of the National Cancer Institute 95:14-18, 2003 can be estimated. For each leave-one-out cross-validation training set, the entire model building process is repeated, including the epigenetic marker selection process. In some instances, it is also evaluated in whether the cross-validated error rate estimate for a model is significantly less than one would expect from random prediction. In some cases, the class labels are randomly permuted and the entire leave-one-out cross-validation process is then repeated. The significance level is the proportion of the random permutations that gives a cross-validated error rate no greater than the cross-validated error rate obtained with the real methylation data.

Another classification method is the greedy-pairs method described by Bo and Jonassen (Genome Biology 3(4): research0017.1-0017.11, 2002). The greedy-pairs approach starts with ranking all markers based on their individual t-scores on the training set. This method attempts to select pairs of markers that work well together to discriminate the classes.

Furthermore, a binary tree classifier for utilizing methylation profile is optionally used to predict the class of future samples. The first node of the tree incorporated a binary classifier that distinguished two subsets of the total set of classes. The individual binary classifiers are based on the "Support Vector Machines" incorporating markers that were differentially expressed among markers at the significance level (e.g. 0.01, 0.05 or 0.1) as assessed by the random variance t-test (Wright G. W. and Simon R. Bioinformatics 19:2448-2455, 2003). Classifiers for all possible binary partitions are evaluated and the partition selected is that for which the cross-validated prediction error is minimum. The process is then repeated successively for the two subsets of classes determined by the previous binary split. The prediction error of the binary tree classifier can be estimated by cross-validating the entire tree building process. This overall cross-validation includes re-selection of the optimal partitions at each node and re-selection of the markers used for each cross-validated training set as described by Simon et al. (Simon et al. Journal of the National Cancer Institute 95:14-

18, 2003). Several-fold cross validation in which a fraction of the samples is withheld, a binary tree developed on the remaining samples, and then class membership is predicted for the samples withheld. This is repeated several times, each time withholding a different percentage of the samples. The samples are randomly partitioned into fractional test sets (Simon R and Lam A. BRB-ArrayTools User Guide, version 3.2. Biometric Research Branch, National Cancer Institute).

Thus, in one embodiment, the correlated results for each marker b) are rated by their correct correlation to the disease, preferably by p-value test. It is also possible to include a step in that the markers are selected d) in order of their rating.

In additional embodiments, factors such as the value, level, feature, characteristic, property, etc. of a transcription rate, mRNA level, translation rate, protein level, biological activity, cellular characteristic or property, genotype, phenotype, etc. can be utilized in addition prior to, during, or after administering a therapy to a patient to enable further analysis of the patient's cancer status.

In some embodiments, a diagnostic test to correctly predict status is measured as the sensitivity of the assay, the specificity of the assay or the area under a receiver operated characteristic ("ROC") curve. In some instances, sensitivity is the percentage of true positives that are predicted by a test to be positive, while specificity is the percentage of true negatives that are predicted by a test to be negative. In some cases, an ROC curve provides the sensitivity of a test as a function of 1-specificity. The greater the area under the ROC curve, for example, the more accurate or powerful the predictive value of the test. Other useful measures of the utility of a test include positive predictive value and negative predictive value. Positive predictive value is the percentage of people who test positive that are actually positive. Negative predictive value is the percentage of people who test negative that are actually negative.

In some embodiments, one or more of the biomarkers disclosed herein show a statistical difference in different samples of at least $p<0.05$, $p<10^{-2}$, $p<10^{-3}$, $p<10^{-4}$ or $p<10^{-5}$. Diagnostic tests that use these biomarkers may show an ROC of at least 0.6, at least about 0.7, at least about 0.8, or at least about 0.9. In some instances, the biomarkers are differentially methylated in different subjects with or without leukemia. In additional instances, the biomarkers for different subtypes of leukemia are differentially methylated. In certain embodiments, the biomarkers are measured in a patient sample using the methods described herein and compared, for example, to predefined biomarker levels and are used to determine whether the patient has leukemia, which leukemia subtype does the patient have, and/or what is the prognosis of the patient having leukemia. In other embodiments, the correlation of a combination of biomarkers in a patient sample is compared, for example, to a predefined set of biomarkers. In some embodiments, the measurement(s) is then compared with a relevant diagnostic amount(s), cut-off(s), or multivariate model scores that distinguish between the presence or absence of leukemia, between leukemia subtypes, and between a "good" or a "poor" prognosis. As is well understood in the art, by adjusting the particular diagnostic cut-off(s) used in an assay, one can increase sensitivity or specificity of the diagnostic assay depending on the preference of the diagnostician. In some embodiments, the particular diagnostic cut-off is determined, for example, by measuring the amount of biomarker hypermethylation or hypomethylation in a statistically significant number of samples from patients with or without leukemia and from patients with different leukemia subtypes, and drawing the cut-off to suit the desired levels of specificity and sensitivity.

Kits/Article of Manufacture

In some embodiments, provided herein include kits for detecting and/or characterizing the methylation profile of a biomarker described herein. In some instances, the kit comprises a plurality of primers or probes to detect or measure the methylation status/levels of one or more samples. Such kits comprise, in some instances, at least one polynucleotide that hybridizes to at least one of the methylation marker sequences described herein and at least one reagent for detection of gene methylation. Reagents for detection of methylation include, e.g., sodium bisulfate, polynucleotides designed to hybridize to sequence that is the product of a marker sequence if the marker sequence is not methylated (e.g., containing at least one C-U conversion), and/or a methylation-sensitive or methylation-dependent restriction enzyme. In some cases, the kits provide solid supports in the form of an assay apparatus that is adapted to use in the assay. In some instances, the kits further comprise detectable labels, optionally linked to a polynucleotide, e.g., a probe, in the kit.

In some embodiments, the kits comprise one or more (e.g., 1, 2, 3, 4, or more) different polynucleotides (e.g., primers and/or probes) capable of specifically amplifying at least a portion of a DNA region of a biomarker described herein. Optionally, one or more detectably-labeled polypeptides capable of hybridizing to the amplified portion are also included in the kit. In some embodiments, the kits comprise sufficient primers to amplify 2, 3, 4, 5, 6, 7, 8, 9, 10, or more different DNA regions or portions thereof, and optionally include detectably-labeled polynucleotides capable of hybridizing to each amplified DNA region or portion thereof. The kits further can comprise a methylation-dependent or methylation sensitive restriction enzyme and/or sodium bisulfite.

In some embodiments, the kits comprise sodium bisulfite, primers and adapters (e.g., oligonucleotides that can be ligated or otherwise linked to genomic fragments) for whole genome amplification, and polynucleotides (e.g., detectably-labeled polynucleotides) to quantify the presence of the converted methylated and or the converted unmethylated sequence of at least one cytosine from a DNA region of an epigenetic marker described herein.

In some embodiments, the kits comprise methylation sensing restriction enzymes (e.g., a methylation-dependent restriction enzyme and/or a methylation-sensitive restriction enzyme), primers and adapters for whole genome amplification, and polynucleotides to quantify the number of copies of at least a portion of a DNA region of an epigenetic marker described herein.

In some embodiments, the kits comprise a methylation binding moiety and one or more polynucleotides to quantify the number of copies of at least a portion of a DNA region of a marker described herein. A methylation binding moiety refers to a molecule (e.g., a polypeptide) that specifically binds to methyl-cytosine.

Examples include restriction enzymes or fragments thereof that lack DNA cutting activity but retain the ability to bind methylated DNA, antibodies that specifically bind to methylated DNA, etc.).

In some embodiments, the kit includes a packaging material. As used herein, the term "packaging material" can refer to a physical structure housing the components of the kit. In some instances, the packaging material maintains sterility of the kit components, and is made of material commonly used for such purposes (e.g., paper, corrugated fiber, glass, plastic, foil, ampules, etc.). Other materials useful in the performance of the assays are included in the kits, including test tubes, transfer pipettes, and the like. In some cases, the kits also include written instructions for the use of one or more of these reagents in any of the assays described herein.

In some embodiments, kits also include a buffering agent, a preservative, or a protein/nucleic acid stabilizing agent. In some cases, kits also include other components of a reaction mixture as described herein. For example, kits include one or more aliquots of thermostable DNA polymerase as described herein, and/or one or more aliquots of dNTPs. In some cases, kits also include control samples of known amounts of template DNA molecules harboring the individual alleles of a locus. In some embodiments, the kit includes a negative control sample, e.g., a sample that does not contain DNA molecules harboring the individual alleles of a locus. In some embodiments, the kit includes a positive control sample, e.g., a sample containing known amounts of one or more of the individual alleles of a locus.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

A "site" corresponds to a single site, which in some cases is a single base position or a group of correlated base positions, e.g., a CpG site. A "locus" corresponds to a region that includes multiple sites. In some instances, a locus includes one site.

EXAMPLES

These examples are provided for illustrative purposes only and not to limit the scope of the claims provided herein.

Example 1

Methylation pattern of CpG sites is an epigenetic regulator of gene expression. Extensive alterations of DNA methylation have been noted in almost all cancer types, causing changes in gene expression that promote oncogenesis. In some instances, changes in a methylation profile are postulated to be reproducibly found in a cancer type. In other instances, somatic mutations are typically neither specific nor sensitive for a particular cancer.

ALL and AML are two types of human acute leukemias (AL), are arising from hematopoietic progenitors of lymphoid or myeloid lineage or from hematopoietic stem cells. In some instances, methylation patterns are utilized to determine presence of leukemia, to differentiate different leukemia subtypes, and to determine a prognosis of a patient having leukemia.

Patient Data

Patient data of AML raining and validation cohorts were obtained from the Cancer Genome Atlas (TCGA). Patient characteristics are summarized in Table 1. Complete clinical, molecular, and histopathological datasets are available at the TCGA website. Individual institutions that contributed samples coordinated the consent process and obtained informed written consent from each patient in accordance to their respective institutional review boards.

A second independent (Chinese) ALL cohort consisted of patients from Guangzhou Women and Children's Medical Center, China and patient characteristics are summarized in Table 1. This project was approved by IRB of Guangzhou Women and Children's Medical Center. Informed consent was obtained from all patients. Tumor and normal tissues were obtained as clinically indicated for patient care and were retained for this study with patients' informed consent.

Data Sources

DNA methylation data were obtained from both the TCGA analysis of 485,000 sites generated using the Infinium 450K Methylation Array and the following GSE datasets: GSE40279, and GSE50192. Methylation profiles for AML cancer type and their corresponding normal blood were analyzed. IDAT format files of the methylation data were generated containing the ratio values of each scanned bead. Using the minfi package from Bioconductor, these data files were converted into a score, referred to as a Beta value. Methylation data of the Chinese cohort was obtained by padlock based bisulfate sequencing of a pan-cancer marker set and analyzed as described below.

A cancer type specific signature was identified via 3 distinct pair-wise comparisons using TCGA samples of the following ten cancers and corresponding normal tissues: lung, breast, colon, liver, brain, kidney, prostate and blood. Methylation difference between a particular cancer type versus its corresponding normal tissue, methylation difference between two different cancer types, as well as methylation difference between two different normal tissues, with a total of 14 tissue groups including 7 tumor groups and 7 normal tissue groups. To do this, a total of 15*14/2=105 unique pair-wise comparisons were performed. Using an Illumina 450,000 CpG methylation microarray, 450 k markers were compared from one group to another group using the [column t test] colttests( ) function in the R genefilter package. Markers were ranked first by lowest p values obtained from t-statistic test and within by largest difference in a mean methylation fraction between each comparison. The top ten markers in each group were selected for further validation analysis. After 105 comparisons, 855 unique, non-redundant markers as a pan-cancer panel were generated.

Classifying Samples

For classifying the ALL, AML and normal blood samples, a supervised learning technique called "nearest shrunken centroids" procedure of Tibshirani et al. (Tibshirani et al., "Diagnosis of multiple cancer types by shrunken centroids of gene expression," *PNAS* 2002; 99: 6567-6572) was applied, which is implemented in the package PAM (Tibshirani et al., "Class prediction by nearest shrunken centroids, with applications to DNA microarrays," *Statistical Science* 2003; 104-117). Specifically, TCGA AML samples, Chinese ALL samples and normal blood samples were first mixed. Seventy percent of these combined samples were put into a training set and thirty percent were put into a validation set. PAM procedures were then performed with 10 fold cross-validation on the training data set and obtained robust classifiers for each AML-normal, ALL-normal and AML-ALL comparison. These classifiers were then used to classify the validation data. This leave-group-out cross-validation was repeated 20 times.

For predicting survival in AML leukemia type, the TCGA AML patient cohort was randomly divided into a training set (n=125) and a validation set (n=55). For each CpG site, a univariate Cox proportional hazard regression model was fit with survival outcome and methylation value as predictors using the training data set. These CpG sites were then ranked based on their Cox scores. 39 CpG sites whose Cox scores exceeded 2.197 were selected. Each patient was then clustered into "good survival" or "bad survival" by 2-means clustering method based on the patients' methylation profiles at these "significant" CpG sites. Log-rank tests on the survival of these two clusters were then conducted. The cutoff Cox score 2.197 (96 percentile of the overall Cox scores) was chosen that resulted in the most significant log-rank test, i.e. the most significant difference in survival between the two clusters. These two optimal clusters were then used to train CpG based classifier for predicting survival in AML subtype by applying PAM and 10-fold cross-validation on the training set. 20 CpG sites were identified and used them as classifiers to predict survival for AML patients in the validation data. Similarly, for predicting survival in ALL leukemia type, the TCGA ALL patient cohort was randomly divided into a training set (n=102) and a validation set (n=34). The CpG sites were also ranked based on their Cox scores. 93 CpG sites whose Cox scores exceeded 3.214986 (92 percentile of the overall Cox scores) were selected. 23 CpG sites were identified and used as classifiers to predict survival for ALL patients in the validation data.

In the analysis, three potential types of classification errors were observed:
False negative; e.g. ALL was identified as normal blood;
False positive; e.g. normal blood was identified as ALL or AML; and
Correct sample, incorrect leukemia type; e.g. ALL was identified as AML.

Tumor DNA Extraction

Genomic DNA extraction from normal blood or ALL bone marrow cancer samples was performed with QIAamp DNA Mini Kit (Qiagen). DNA was stored at −20° C. and analyzed within one week of preparation.

Bisulfite Conversion of Genomic DNA

Up to 1 µg of genomic DNA was converted to bis-DNA using EZ DNA Methylation-Lightning™ Kit (Zymo Research). Resulting bis-DNA had a size distribution of ~200-3000 bp, with a peak around ~500-1000 bp. The efficiency of bisulfite conversion was >99.8% as verified by deep-sequencing of bis-DNA and analyzing the ratio of C to T conversion of CH (non-CG) dinucleotides.

Determination of DNA Methylation Levels of the ALL Cohort by Deep Sequencing of Bis-DNA Captured with Molecular-Inversion (Padlock) Probes CpG markers whose methylation levels differed in any of the comparison between and normal tissue were used to design padlock probes for sequencing. Padlock-capture of bis-DNA was based on published techniques and protocols with the following modifications.

Determination of DNA Methylation Levels by Deep Sequencing of Bis-DNA Captured with Molecular-Inversion (Padlock) Probes Padlock probes were designed to capture regions containing the CpG markers whose methylation levels differed in comparison between leukemia and normal blood. Padlock-capture of bis-DNA was based on published techniques and protocols with modifications.

Probe Design and Synthesis

Padlock probes were designed using the ppDesigner software. The average length of the captured region was 70 bp, with the CpG marker located in the central portion of the captured region. To prevent bias introduced by unknown methylation status of CpG markers, capturing arms were positioned exclusively within sequences devoid of CG dinucleotides. Linker sequence between arms contained binding sequences for amplification primers separated by a variable stretch of Cs to produced probes of equal length. The average length of probes was 91 bp. Probes incorporated a 6-bp unique molecular identifier (UMI) sequence to allow for the identification of individual molecular capture events and accurate scoring of DNA methylation levels.

Probes were synthesized as separate oligonucleotides using standard commercial synthesis methods. For capture experiments, probes were mixed, in-vitro phosphorylated with T4 PNK (NEB) according to manufacturer's recommendations and purified using P-30 Micro Bio-Spin columns (Bio-Rad).

Bis-DNA Capture 20 ng of bisulfite-converted DNA was mixed with a defined molar ratio of padlock probes in 20 µl reactions containing 1× Ampligase buffer (Epicentre). Reactions were covered with 50 µl of mineral oil to prevent evaporation. To anneal probes to DNA, 30 second denaturation at 95° C. was followed by a slow cooling to 55° C. To fill gaps between annealed arms, the following mixture was added to each reaction: 2 U of PfuTurboCx polymerase (Agilent), 0.5 U of Ampligase (Epicentre) and 250 pmol of each dNTP in 1× Ampligase buffer. After 5 hour incubation at 55° C., reactions were denatured for 2 minutes at 94° C. and snap-cooled on ice. Exonuclease mix (20 U of Exo I and 100 U of ExoIII, both from Epicentre) was added and single-stranded DNA degradation was carried out at 37° C. for 2 hours, followed by enzyme inactivation for 2 minutes at 94° C.

Circular products of site specific capture were amplified by PCR with concomitant barcoding of separate samples. Amplification was carried out using primers specific to linker DNA within padlock probes, one of which contained specific 6 bp barcodes. Both primers contained Illumina next-generation sequencing adaptor sequences. PCR of the captured DNA was performed using Phusion Flash Master Mix (Thermo), and 200 nM final concentration of primers, under the following cycle conditions: 10 s @ 98° C., 8× of (1 s @ 98° C., 5 s @ 58° C., 10 s @ 72° C.), 25× of (1 s @ 98° C., 15 s @ 72° C.), 60 s @ 72° C. PCR reactions were mixed and the resulting library was size selected to include effective captures (~230 bp) and exclude "empty" captures (~150 bp) using Agencourt AMPure XP beads (Beckman Coulter). Purity of the libraries was verified by PCR using Illumina flowcell adaptor primers (P5 and P7) and the concentrations were determined using Qubit dsDNA HS assay (Thermo Fisher). Libraries we sequenced using MiSeq and HiSeq2500 systems (Illumina).

Optimization of Capture Coverage Uniformity

Deep sequencing of the original pilot capture experiments showed significant differences between number of reads captured by most efficient probes and non-efficient probes (60-65% of captured regions with coverage >0.2 of average). To ameliorate this, relative efficiencies were calculated from sequencing data and probes were mixed at adjusted molar ratios. This increased capture uniformity to 85% of regions at >0.2 of average coverage.

Sequencing Data Analysis

Mapping of sequencing reads was done using the software tool bisReadMapper (Diep et al. "Library-free methylation sequencing with bisulfite padlock probes," *Nature Methods* 2012; 9: 270-272) with some modifications. First, UMI were extracted from each sequencing read and appended to read headers within FASTQ files using a custom script generously provided by D. D. Reads were on-the-fly converted as if all C were non-methylated and mapped to in-silico converted DNA strands of the human genome, also as if all C were non-methylated, using Bowtie2 (Langmead et al., "Fast gapped-read alignment with Bowtie 2," *Nature Methods* 2012; 9: 357-359). Original reads were merged and filtered for single UMI, i.e. reads carrying the same UMI were discarded leaving a single one. Methylation frequencies were extracted for all CpG markers for which padlock probes were designed. Markers with less than 20 reads in any sample were excluded from analysis. This resulted in ~600 CpG markers for which the methylation level was determined with the accuracy of 5% or more.

Characteristics of Patients

Clinical characteristics and molecular profiling including methylation data for the study cohort were obtained for 194 AML patients, 136 ALL patients, and 754 healthy individuals. Clinical characteristics of the AML and ALL patients in study cohorts and healthy controls are listed in Table 1.

Genome Wide Methylation Profiling Identified Specific Methylation Signatures in Leukemia The TCGA AML samples, Chinese ALL samples and normal blood samples of healthy controls were randomly split by 70/30 split into training and validation data sets using R. The methylation differences were then compared between TCGA AML samples and normal blood samples, Chines ALL samples and normal blood samples in training data sets using nearest shrunken centroids method. Two sets of CpG sites were then identified and used to differentiate TCGA AML samples from normal blood samples, and Chines ALL samples from normal blood samples, in the validation data sets, respectively. Such random splitting was repeated 20 times. Table 2A, 2B demonstrated a confusion table describing the performance of these classifiers to differentiate AML and ALL samples from normal blood samples on one of the 20 validation data sets (Table 3). The 20 sets of CpG sites identified through AML-normal comparison revealed 4 common CpG sites. These four CpG sites were plotted in an unsupervised fashion in AML versus normal blood samples (FIG. 1A). The accuracy of using these four CpG sites for predicting the AML leukemia can be assessed by the ROC curve (FIG. 1B) with AUC of 0.9998.

Figure 1B:
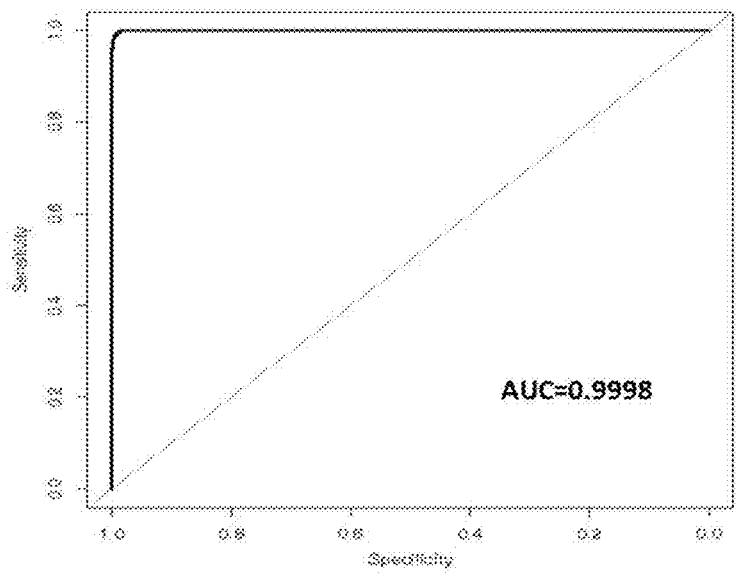
Figure 2A:
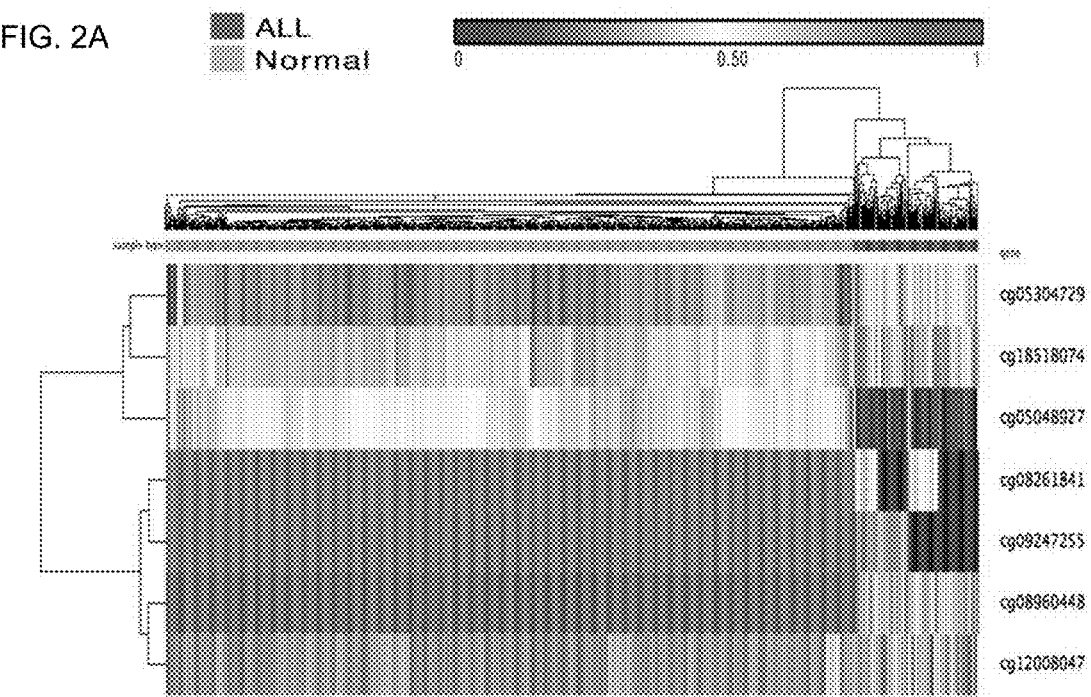
FIG. 2A-FIG. 2B illustrate a methylation profile of ALL in comparison to normal blood.
Figure 2B:
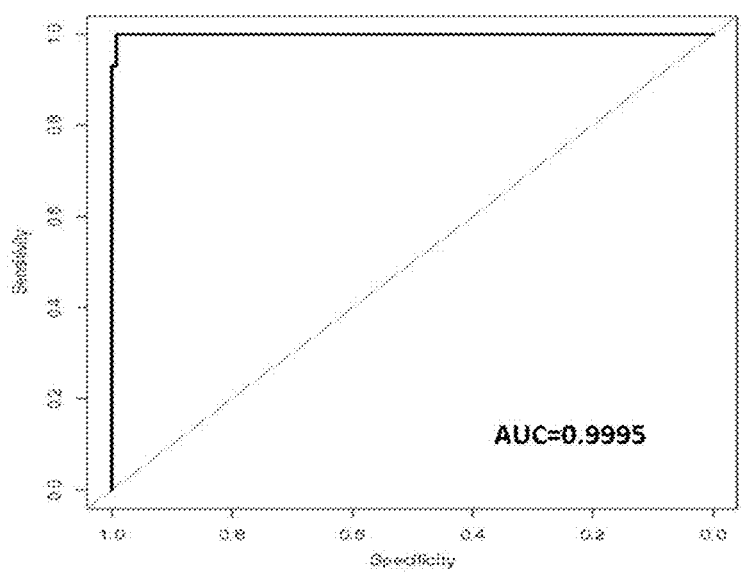

Similarly, 7 common CpG sites were identified through ALL-normal comparison (FIG. 2A). The accuracy of using these seven CpG sites for predicting the ALL leukemia can be assessed by the ROC curve (FIG. 2B) with AUC of 0.9995. It is noted that 2 common CpG sites (cg05304729 and cg18518074) appeared both in AML-normal comparison and in ALL-normal comparison (FIGS. 1A and 2A). Taken together, these data demonstrated that differential methylation of CpG sites was able to distinguish a particular leukemia type from normal blood with high specificity and sensitivity (FIGS. 1B and 2B).

Methylation Profiles can Distinguish Between Different Leukemia

Figure 3A:
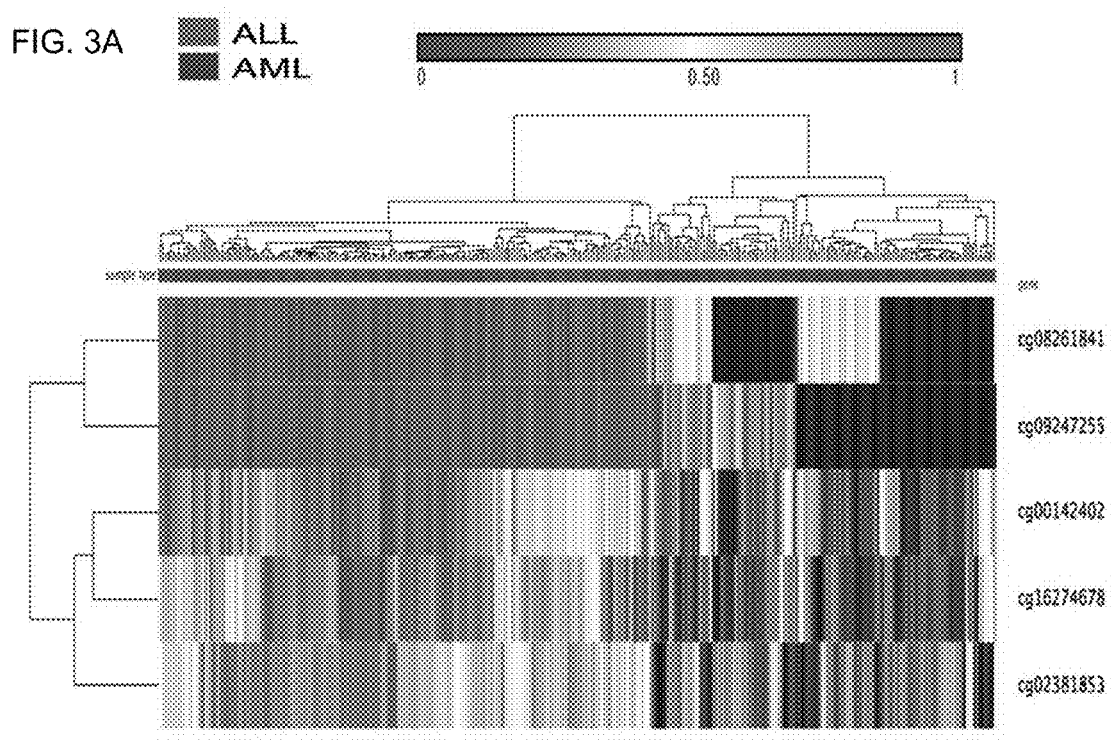
FIG. 3A-FIG. 3B show a methylation profile of ALL and AML subtypes of five markers. Unsupervised hierarchical clustering and heatmap with the methylation profile (according to the color scale shown) in ALL versus AML samples is illustrated in FIG. 3A.
Figure 3B:
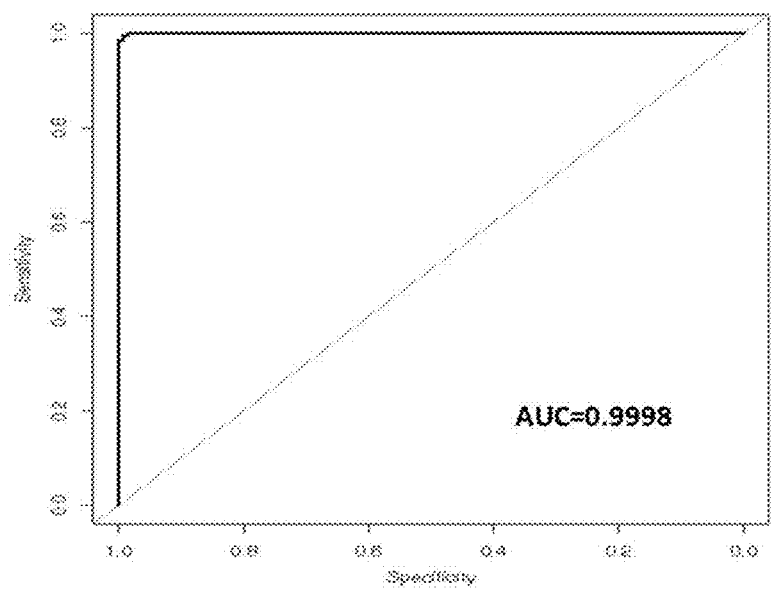
Figure 4:
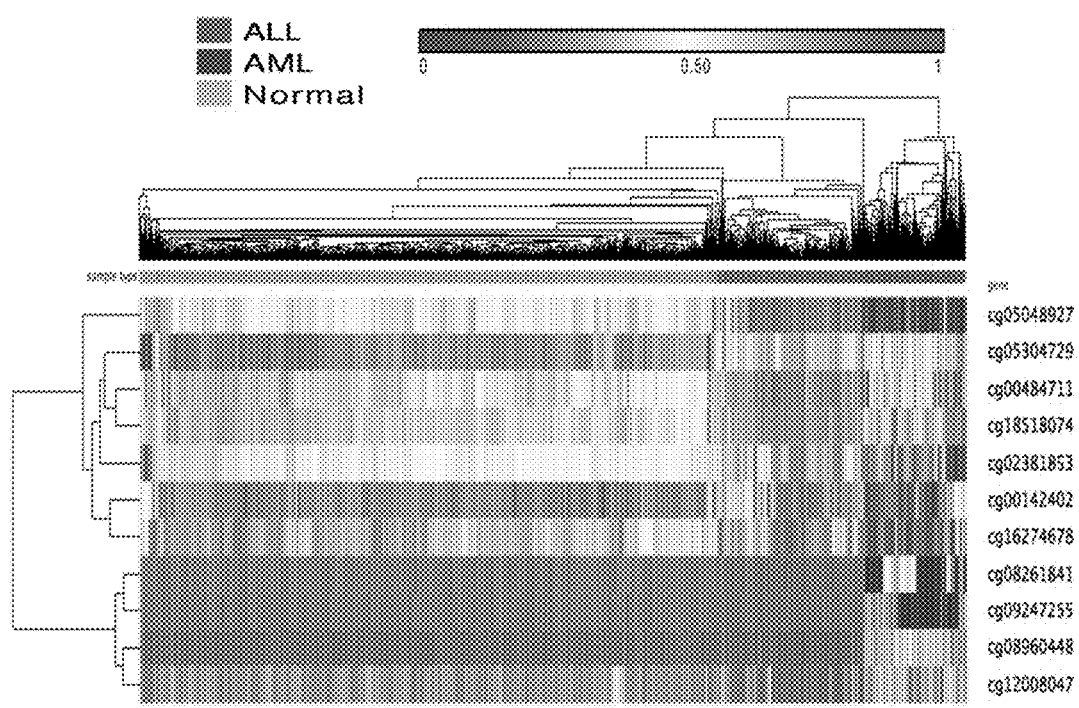
FIG. 4 shows a methylation profile comparison of ALL, AML, and normal blood. The methylation profile of 11 markers shows differences between ALL, AML, and normal blood. Unsupervised hierarchical clustering and heatmap associated with ALL, AML and normal blood.

Next, it was investigated in whether different subtypes of leukemic cancers (e.g., ALL and AML) would be identified from bone marrow samples. 5 CpG sites were identified to be used to differentiate TCGA AML samples from the Chinese ALL samples (FIG. 3A). Table 2C describes the performance of the classifiers on one of 20 validation data sets consisting of the TCGA AML samples and the Chinese ALL cohort samples used in Table 2A, 2B. It is noted that among these 5 CpG sites, one (cg00142402) was also identified in AML and normal comparison and two (cg08261841 and cg09247255) were also identified in ALL and normal comparison. The accuracy of using these five CpG sites to differentiate between the AML and ALL leukemia were assessed by the ROC curve (FIG. 3B) with AUC of 0.9998. Together, these results demonstrate the efficacy of using methylation patterns for accurate cancer diagnosis of a histological subtype. The 11 unique CpG sites that can differentiate among TCGA AML, Chinese ALL and normal blood samples were plotted in an unsupervised fashion in FIG. 4.

Methylation Profiles Predict Prognosis and Survival Rates

Figure 6A:
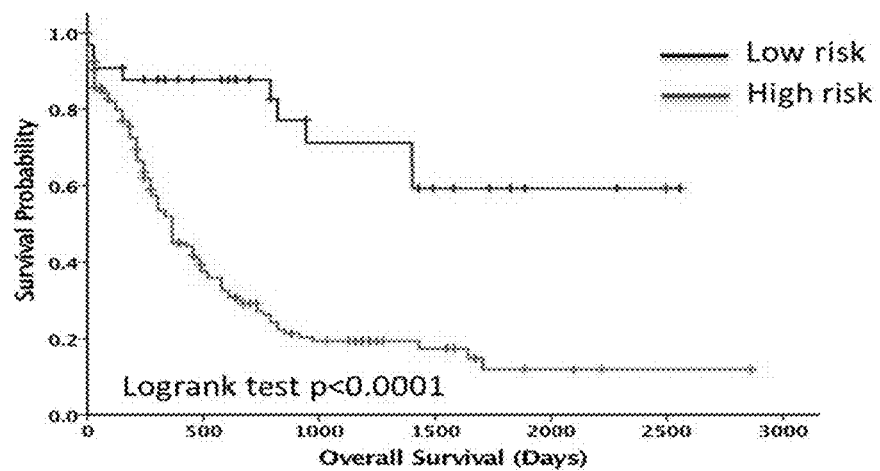
FIG. 6A-FIG. 6B illustrate a five-year overall survival of patients based on methylation markers.
Figure 6B:
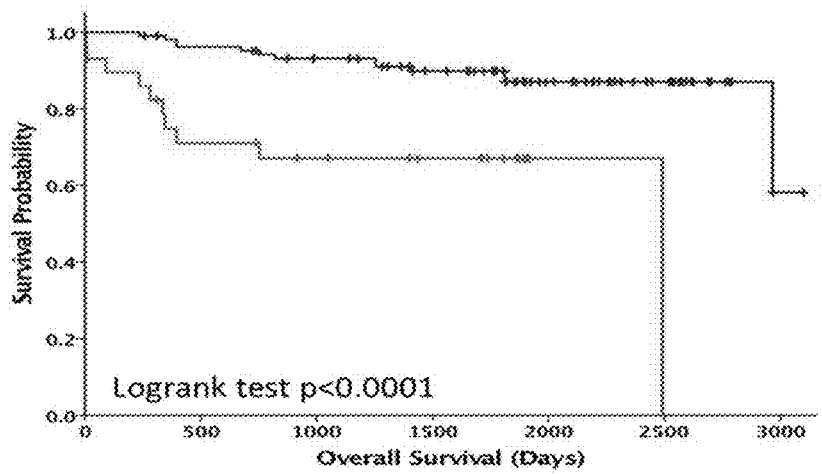

The effect of methylation markers on survival rate of each leukemia subtype (AML and ALL) based on a semi-supervised method (Bair E, Tibshirani R. "Semi-supervised methods to predict patient survival from gene expression data," *PLoS Biol* 2004; 2: E108) were investigated and a list of 20 and 23 methylation signatures that correlated with patient survival (specifically, alive vs dead at a 5-year period from time of diagnosis) for AML subtype and ALL subtype were identified, respectively. For each leukemic type, samples in the validation cohort were divided into two groups based on the above methylation signatures and individual patient survival data were plotted using a Kaplan-Meier curve (FIG. 5 and FIG. 6). In some instances, these methylation profiles were used to predict differences in survival of patients with ALL and AML.

TABLE 1

Clinical characteristics

| Characteristic | AML | ALL | Normal |
|---|---|---|---|
| Total (n) | 194 | 136 | 754 |
| Gender | | | |
| Femal-no.(%) | 90(46) | 42(31) | 401(53) |
| Male-no.(%) | 104(54) | 94(69) | 353(47) |
| Age at diagnosis-yr | | | |
| Midian | 55 | 5 | 63 |
| Range | 18-88 | 1-13 | 19-101 |
| White race-no/total no.(%) | | | |
| White | 176(91) | 0 | 504(67) |
| Asian | 2(1) | 136(100) | 7(1) |
| Other | 16(8) | 0 | 243(32) |
| White cell count at diagnosis (×10$^9$/L) | | | |
| Mean | 37.94 ± 30.72 | 8.15 ± 5.78 | NA |
| Median | 17 | 5 | NA |

TABLE 1-continued

Clinical characteristics

| Characteristic | AML | ALL | Normal |
|---|---|---|---|
| FAB subtype - no. (%) | | | |
| AML with minimal maturation: M0 | 19(10) | NA | NA |
| AML without maturation: M1 | 42(22) | NA | NA |
| AML with maturation: M2 | 43(22) | NA | NA |
| Acute promyelocytic leukemia: M3 | 19(10) | NA | NA |
| Acute myelomonocytic leukemia: M4 | 41(21) | NA | NA |
| Acute monoblastic or monocytic leukemia: M5 | 22(11) | NA | NA |
| Acute erythroid leukemia: M6 | 3(1.5) | NA | NA |
| Acute megakaryoblastic leukemia: M7 | 3(1.5) | NA | NA |
| ALL-L1 | NA | 74(55) | NA |
| ALL-L2 | NA | 37(27) | NA |
| ALL-L3 | NA | 14(10) | NA |
| Other subtype | 2(1) | 11(8) | NA |
| Cytogenetic risk group-no (%) | | | |
| Favorable | 36(19) | 19(14) | NA |
| Intermediate | 110(57) | 64(47) | NA |
| Unfavorable | 43(22) | 39(29) | NA |
| Missing data | 3(2) | 14(10) | NA |

ALL-L1: Small cells with homogeneous nuclear chromatin, a regular nuclear shape, small or no nucleoli, scanty cytoplasm, and mild to moderate
ALL-L2: Large, heterogeneous cells with variable nuclear chromatin, an irregular nuclear shape, 1 or more nucleoli, a variable amount of cytoplasm, and variable basophilia
ALL-L3: Large, homogeneous cells with fine, stippled chromatin; regular nuclei; prominent nucleoli; and abundant, deeply basophilic cytoplasm. The most distinguishing feature is prominent cytoplasmic vacuolation

TABLE 2A

Training Cohort-AML

| Training Cohort | AML | Normal Blood | Totals |
|---|---|---|---|
| AML | 134 | 1 | |
| Normal Blood | 1 | 526 | |
| Totals | 135 | 527 | 662 |
| Correct | 134 | 526 | 660 |
| False Positive | 0 | 1 | 1 |
| False Negative | 1 | 0 | 1 |
| Specificity (%) | | 99.8 | 99.8 |
| Sensitivity (%) | 99.3 | | 99.3 |

TABLE 2B

Training Cohort-ALL

| Training Cohort | ALL | Normal Blood | Totals |
|---|---|---|---|
| ALL | 94 | 0 | |
| Normal Blood | 1 | 527 | |
| Totals | 95 | 527 | 662 |
| Correct | 94 | 527 | 661 |
| False Positive | 0 | 0 | 0 |
| False Negative | 1 | 0 | 1 |
| Specificity (%) | | 100 | 99.8 |
| Sensitivity (%) | 98.9 | | 98.9 |

TABLE 2C

Training Cohort-AML and ALL

| Training Cohort | AML | ALL | Totals |
|---|---|---|---|
| AML | 135 | 0 | |
| Normal Blood | 0 | 95 | |
| Totals | 135 | 95 | 230 |
| Correct | 135 | 95 | 230 |
| False Positive | 0 | 0 | 0 |
| False Negative | 0 | 0 | 0 |
| Specificity (%) | | 100 | 100 |
| Sensitivity (%) | 100 | | 100 |

TABLE 3A

Validation Cohort-AML

| Training Cohort | AML | Normal Blood | Totals |
|---|---|---|---|
| AML | 59 | 6 | |
| Normal Blood | 0 | 221 | |
| Totals | 59 | 227 | 286 |
| Correct | 59 | 221 | 280 |
| False Positive | 0 | 6 | 6 |
| False Negative | 0 | 0 | 0 |
| Specificity (%) | | 97.4 | 97.4 |
| Sensitivity (%) | 100 | | 100 |

TABLE 3B

Validation Cohort-ALL

| Training Cohort | ALL | Normal Blood | Totals |
|---|---|---|---|
| ALL | 41 | 0 | |
| Normal Blood | 0 | 227 | |
| Totals | 41 | 227 | 268 |
| Correct | 41 | 227 | 268 |
| False Positive | 0 | 0 | 0 |
| False Negative | 0 | 0 | 0 |
| Specificity (%) | | 100 | 100 |
| Sensitivity (%) | 100 | | 100 |

TABLE 3C

Validation Cohort-AML and ALL

| Training Cohort | AML | ALL | Totals |
|---|---|---|---|
| AML | 59 | 0 | |
| Normal Blood | 0 | 41 | |
| Totals | 59 | 41 | 100 |
| Correct | 59 | 41 | 100 |
| False Positive | 0 | 0 | 0 |
| False Negative | 0 | 0 | 0 |
| Specificity (%) | | 100 | 100 |
| Sensitivity (%) | 100 | | 100 |

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of detecting a methylation pattern of a set of biomarkers in a subject suspected of having leukemia, the method comprising:
   a) processing an extracted genomic DNA with a deaminating agent to generate a genomic DNA sample comprising deaminated nucleotides, wherein the extracted genomic DNA is obtained from a biological sample from the subject suspected of having leukemia; and
   b) detecting the methylation pattern of one or more biomarkers selected from: cg08261841, cg09247255, cg00142402, cg16274678, and cg02381853 from the extracted genomic DNA by contacting the extracted genomic DNA with a set of probes, wherein the set of probes hybridizes to the one or more biomarkers, and perform a DNA sequencing analysis to determine the methylation pattern of the one or more biomarkers.

2. The method of claim 1, wherein step b) comprises detecting the methylation pattern of cg08261841, cg09247255, cg00142402, cg16274678, and cg02381853.

3. The method of claim 1, further comprising detecting a methylation pattern of a biomarker selected from: cg05304729, cg00484711, cg18518074, cg05048927, cg08960448, and cg12008047.

4. The method of claim 1, wherein the method comprises detecting the methylation of cg08261841, cg09247255, cg00142402, cg16274678, cg02381853, cg05304729, cg00484711, cg18518074, cg05048927, cg08960448, and cg12008047.

5. The method of claim 1, wherein the biological sample comprises a blood sample.

6. The method of claim 1, wherein the biological sample comprises a tissue biopsy sample.

7. The method of claim 1, wherein the biological sample comprises circulating tumor cells.

8. The method of claim 1, wherein the subject is a human.

9. The method of claim 1, wherein each probe from the set of probes is a padlock probe.

10. A method of detecting a methylation pattern of a set of biomarkers in a subject suspected of having acute lymphoblastic leukemia (ALL), comprising:
    a) processing an extracted genomic DNA with a deaminating agent to generate a genomic DNA sample comprising deaminated nucleotides, wherein the extracted genomic DNA is obtained from a biological sample from the subject; and
    b) detecting the methylation pattern of biomarkers cg08261841, cg09247255, cg12008047, cg05304729, cg18518074, cg05048927, and cg08960448 from the extracted genomic DNA by contacting the extracted genomic DNA with a set of probes, wherein the set of probes hybridizes to the one or more biomarkers, and perform a DNA sequencing analysis to determine the methylation pattern of the one or more biomarkers.

11. The method of claim 10, wherein each probe from the set of probes is a padlock probe.

12. The method of claim 10, wherein the biological sample comprises a blood sample.

13. The method of claim 10, wherein the biological sample comprises a tissue biopsy sample.

14. The method of claim 10, wherein the biological sample comprises circulating tumor cells.

15. The method of claim 10, wherein the subject is a human.

16. A method of detecting a methylation pattern of a set of biomarkers in a subject suspected of having acute myeloid leukemia (AML), comprising:
    a) processing an extracted genomic DNA with a deaminating agent to generate a genomic DNA sample comprising deaminated nucleotides, wherein the extracted genomic DNA is obtained from a biological sample from the subject; and
    b) detecting the methylation pattern of biomarkers cg00142402, cg05304729, cg00484711, and cg18518074 from the extracted genomic DNA by contacting the extracted genomic DNA with a set of probes, wherein the set of probes hybridizes to the one or more biomarkers, and perform a DNA sequencing analysis to determine the methylation pattern of the one or more biomarkers.

17. The method of claim 16, wherein each probe from the set of probes is a padlock probe.

18. The method of claim 16, wherein the biological sample comprises a blood sample.

19. The method of claim 16, wherein the biological sample comprises a tissue biopsy sample.

20. The method of claim 16, wherein the biological sample comprises circulating tumor cells.

21. The method of claim 16, wherein the subject is a human.

* * * * *